United States Patent [19]

Walsh et al.

[11] Patent Number: 5,061,720

[45] Date of Patent: Oct. 29, 1991

[54] SUBSTITUTED-4-THIAZOLIDINONE DERIVATIVES

[75] Inventors: David A. Walsh, Richmond; Ibrahim M. Uwaydah, Chesterfield, both of Va.

[73] Assignee: A.H. Robins Company, Inc., Richmond, Va.

[21] Appl. No.: 406,579

[22] Filed: Sep. 13, 1989

[51] Int. Cl.$^5$ ................ A61K 31/425; C07D 277/04
[52] U.S. Cl. .................... 514/369; 514/886; 514/887; 548/182; 548/186; 548/187; 548/188; 548/200; 548/201
[58] Field of Search ............ 548/200, 201, 186, 187, 548/188, 182; 514/369, 886, 887

[56] References Cited

U.S. PATENT DOCUMENTS

| | | | |
|---|---|---|---|
| 2,520,178 | 8/1950 | Surrey | 548/182 X |
| 2,623,048 | 12/1952 | Long | 548/182 |
| 3,006,919 | 10/1961 | Gaul et al. | 548/182 |
| 4,664,694 | 5/1987 | Brouwer et al. | 548/182 X |

Primary Examiner—Catherine S. Kilby Scalzo
Attorney, Agent, or Firm—Richard K. Jackson

[57] ABSTRACT

Disclosed are novel substituted 4-thiazolidinone derivatives having cyclooxygenase and 5-lipoxygenase inhibiting properties and which are topical antiinflammatory agents for inflamed conditions of the skin having the formula:

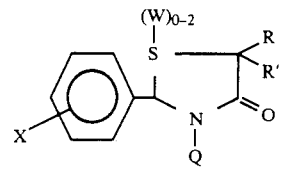

wherein R is hydrogen or loweralkyl; $R^1$ is loweralkyl or aryl; X is —($CH_2$)-aryl, —O—($CH_2$)$_{0-3}$-aryl, —C(O)($CH_2$)$_{0-3}$-aryl, —CH(OH)—($CH_2$)$_{0-3}$-aryl or 3,4

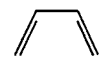

(to form naphthyl ring); aryl is phenyl, substituted phenyl, or 2,3 or 4 pyridyl; W is oxygen; Q is -(alk$^1$)$_{0-1}$—(O)$_{0-1}$—(B)$_{0-1}$—(alk$^2$)$_{0-1}$—[C(O)Z]$_{0-1}$; B is

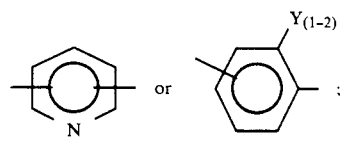

Z is OR$^3$ or NR$^4$R$^5$ where R$^3$ is hydrogen, loweralkyl, or a pharmaceutically acceptable metal cation, R$^4$ and R$^5$ are hydrogen or loweralkyl; alk$^1$ and alk$^2$ are lower alkylene or loweralkyleneloweralkyl, Y is hydrogen, loweralkyl, loweralkoxy, trifluoromethyl, nitro, or halo; and the stereoisomers and optical isomers thereof and pharmaceutically acceptable acid addition salts which form when a basic nitrogen is present.

31 Claims, No Drawings

SUBSTITUTED-4-THIAZOLIDINONE DERIVATIVES

BACKGROUND OF THE INVENTION

1. Field of Invention

The present invention relates to certain novel substituted 4-thiazolidinone derivatives which exhibit cyclooxygenase and lipoxygenase inhibition activity in warm blooded animals. The invention is also concerned with methods of and compositions for treating inflammation topically, particularly in treatment of inflammed conditions of the skin such as sunburn, psoriasis, eczema, seborrhea and the like.

2. Information Disclosure Statement

Synthesis of 4-thiazolidinones substituted in the 3-position by a pyridyl radical and in the 2-position by a substituted phenyl radical was reported by D. R. Patel, et al. in Vidya. B. Sciences Vol. XX(1) 95–97 (January 1977) which 4-thiazolidinones are illustrated by the formula:

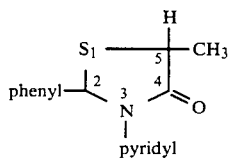

wherein phenyl is substituted by 2,4-dichloro or by 4-methoxy. In contrast, the compounds of the present invention are substituted on phenyl by larger entities such as phenoxy, etc. No pharmaceutical utility was disclosed.

Japanese workers have reported in Japan. Kokai Tokkyo Koho JP 57 88, 170 [8288, 170] (1982) see Chem. Abstr. 98, 53872r that certain substituted 4-thiazolidinones have antiinflammatory and analgesic activities. These compounds have a phenylacetic acid moiety in the 3 position similar to some compounds of the present invention. Again in comparison, the compounds of the present invention are different, having expanded aryl moieties in the 2 position.

Certain 4-thiazolidinones substituted in the 2 position by a phenylacetic acid-loweralkyl group have been disclosed in U.S. Pat. No. 4,225,609 as having use in treating hypertension, renal failure, congestive heart failure, glomerulonephritis, uremia and chronic renal insufficiency.

SUMMARY OF THE INVENTION

The novel substituted 4-thiazolidinone compounds of this invention have the formula:

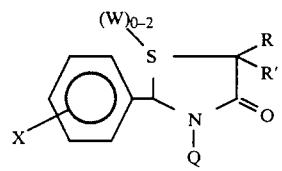

Formula I wherein:
R is hydrogen or loweralkyl;
R' is loweralkyl or aryl;
X is —(CH$_2$)$_{0-3}$-aryl, —O(CH$_2$)$_{0-3}$-aryl, —C(O)(CH$_2$)$_{0-3}$-aryl, —CHOH—(CH$_2$)$_{0-3}$-aryl or 3,4-

(ring to form naphthyl), aryl is phenyl, substituted phenyl, or 2, 3, or 4-pyridyl;
W is oxygen;
Q is —(alk$^1$)$_{0-1}$—(O)$_{0-1}$—(B)$_{0-1}$—(O)$_{0-1}$—(alk$^2$)$_{0-1}$—[C(O)Z]$_{0-1}$;

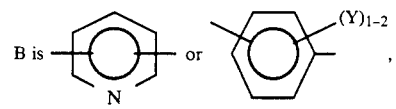

Y is selected from hydrogen, loweralkyl, loweralkoxy, trifluoromethyl, nitro, or halo;
alk$^1$ and alk$^2$ are selected from the group consisting of loweralkylene or loweraklylene-loweralkyl and may be the same or different;
Z is —OR$^3$ or —NR$^4$R$^5$,
R$^3$ is hydrogen, loweralkyl or a pharmaceutically acceptable metal cation;
R$^4$ and R$^5$ are hydrogen or loweralkyl;
and when any of the groups within the definition of Q other than [C(O)Z] is a terminal group, the valence is occupied by a hydrogen atom;
and the cis and trans stereoisomers and the optically active isomers thereof and pharmaceutically acceptable acid addition salts which form when a basic nitrogen moiety is present.

The term "loweralkylene" as used herein refers to connecting hydrocarbon groups represented by methylene (—CH$_2$—), ethylene (—CH$_2$—CH$_2$—) propylene (—CH$_2$—CH$_2$—CH$_2$—) and the like. The term "loweralkyl-loweralkylene" is represented by hydrocarbon groups such as ethylidene

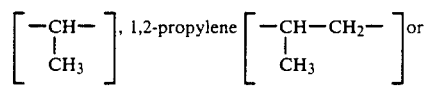

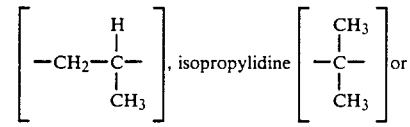

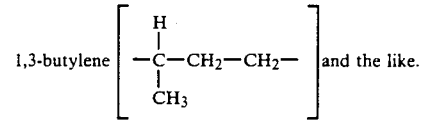

The term "loweralkyl" as used herein includes straight and branched chain radicals of up to eight carbons inclusive and is exemplified by such groups as methyl, ethyl, propyl, isopropyl, isobutyl, butyl, amyl, isoamyl, hexyl, heptyl, and octyl radicals and the like. Tertiary alkyl radicals are excluded from the definition of loweralkyl.

The term substituted phenyl as used herein refers to a phenyl radical substituted by any radical or radicals which are not reactive or otherwise noninterfering under the conditions of preparation reactions, such radicals including loweralkyl, loweralkoxy, trifluoromethyl, halo, nitro, and the like, one to three such radicals may be present and may be in various positions on the benzene ring. By "halo" is meant fluoro, chloro, bromo, and iodo radicals.

The term "pharmaceutically acceptable metal cation" refers to metal cations derived from such as alkali metals, alkaline earth metals, aluminum, iron and zinc. Especially preferred metal cations are those derived from alkali metals, e.g., sodium, potassium, lithium and the like and alkaline earth metals, e.g., calcium, magnesium and the like.

The methods relied upon to determine efficacy of the compounds as topical anti-inflammatory agents involve demonstration in vitro inhibition of the enzymes cyclooxygenase and 5-lipoxygenase in tissue preparations incubated together with arachidonic acid and reduction in erythema when applied after exposure of live guinea pig skin to ultraviolet light as explained in detail hereinbelow under Pharmacological Test Procedures.

The present invention encompasses the methods of use of the compounds of Formula I in transdermal administration to animals and humans for the treatment of inflammation and pharmaceutical compositions therefore suitable for external application to a live animal body.

In the method of this invention, the compounds of Formula I are applied externally to the skin of animals and humans in the form of creams, lotions, ointments, solutions, suspensions or foams. The rate of delivery may be modified or controlled by composition of matrix and by chemical enhancers. The carriers and methods of administration are discussed more in detail hereinbelow.

DETAILED DESCRIPTION OF THE INVENTION

The substituted 4-thiazolidinones of Formula I are prepared by reacting a mixture of an appropriate aryl aldehyde, an appropriate primary amine and an appropriate α-mercaptocarboxylic and, followed by oxidizing, if required, as represented by equation in Chart I.

CHART I

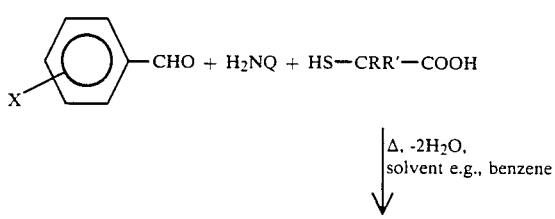

$\Delta$, -2H$_2$O,
solvent e.g., benzene

-continued
CHART I

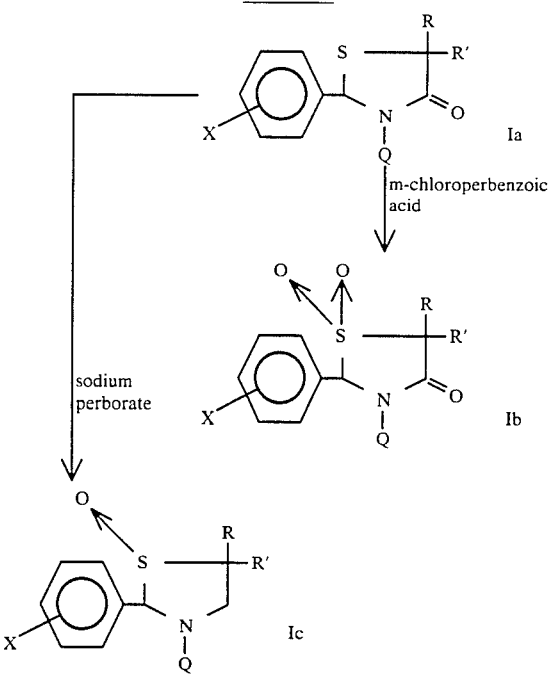

Compounds of Formula Ia so prepared wherein Q contains an ester moiety, i.e., Z=O-loweralkyl may be de-esterified, if desired, by usual methods known in the art by heating in aqueous alkali metal base to give the corresponding metal carboxylic acid salt. The salt may then be acidified to produce compounds wherein Z=OH. Conversion of such acid compounds so produced to other metal salts may be accomplished by reacting with an appropriate metal base in an aprotic solvent. Compounds of Formula Ia, Ib, and Ic and these salts are encompassed by Formula I.

The starting aldehydes, if not commercially available, can be prepared by standard chemical procedures. The primary amines, if not commercially available, can be prepared by standard chemical procedures. The α-mercaptocarboxylic acids, if not commercially available, can be prepared by literature procedures. The procedure of B. H. Nicolet and L. F. Bate, J. Amer. Chem. Soc. (1927) 49, 2064-2066 is an example of such procedures represented as follows:

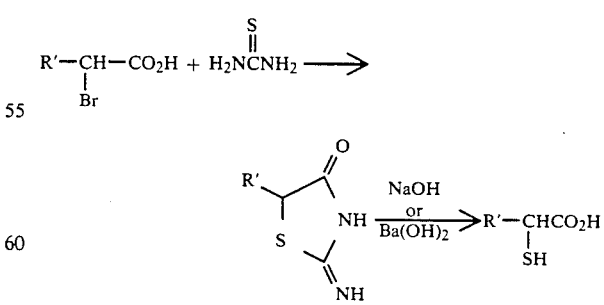

Commercial suppliers of the starting materials were:
1. Aldrich Chemical Company, P.O. Box 2060, Milwaukee, Wis. 53201.
2. J. T. Baker Chemical Company, 222 Red School Lane, Phillipsburg, N.J. 08865.

3. Columbia Organic Chemical Company, Inc., P.O. Box 1045, Camden, S.C. 29020.
4. Fluka Chemical Corporation, 980 South Second Street, Ronkonkoma, N.Y. 11779.

The following preparations and examples are provided merely by way of illustrating the methods of preparation and the compounds and are not to be construed as being limiting in nature.

PREPARATION 1

4-(3-Chloropropoxy)benzoic acid ethyl ester.

Ethyl 4-hydroxybenzoate (0.50 mole, 83.1 g), 1-bromo-3-chloropropane (1.0 mole, 107.1 mL) and potassium carbonate (1.5 mole, 207.3 g) were mechanically stirred in refluxing acetone (600 mL) under nitrogen atmosphere overnight. The potassium carbonate was removed by filtration, and the filtrate was evaporated under reduced pressure to give 122 g of a liquid. This liquid was dissolved in 250 mL of petroleum ether, and the solution was stirred and cooled in an ice/2-propanol bath, and a white precipitate formed. The solid was collected by filtration and washed with cold petroleum ether to yield 108 g of a solid. An additional 6 g of solid was obtained from the mother liquor.

A small sample (0.5 g) of the solid was dissolved in petroleum ether at room temperature. The solution was stirred and cooled in an ice bath. The white crystals that formed were collected by filtration, washed with cold petroleum ether and dried under vacuum at room temperature to yield title compound, mp 24°–25° C.

| Analysis calculated for: | $C_{12}H_{15}ClO_3$: C,59.39;H,6.23 |
|---|---|
| | Found: C,59.69;H,6.30 |

PREPARATION 2

4-[3-(1,3-Dihydro-1,3-dioxo-2H-isoindol-2-yl)propoxy]benzoic acid ethyl ester.

To a stirred solution of 22.5 g (0.092 mole) of 4-(3-chloropropoxy)benzoic acid ethyl ester in 150 mL of dimethylformamide was added 17.6 g (0.093 mole) of potassium phthalimide (98%, Aldrich) and the mixture was heated (135° C.) under a nitrogen atmosphere for 8 hr. The solvent was evaporated under reduced pressure to leave a semi-solid residue. The residue was triturated with 100 mL of water and the resulting solid was collected by filtration. The solid was recrystallized from isopropyl alcohol to yield 18.2 g (55%) of title compound as an off-white solid, mp 106°–108° C.

| Analysis calculated for: | $C_{20}H_{19}NO_5$: C,67.98;H,5.42;N,3.96 |
|---|---|
| | Found: C,67.80;H,5.27;N,4.29 |

PREPARATION 3

2-(5-Phenylpentyl)-1,3-dihydro-1,3-dioxo-2H-isoindole.

To a stirred solution of 24.0 g (0.131 mole) of 1-chloro-5-phenylpentane (Columbia Organics, Camden, S.C.) in 150 mL of dimethylformamide was added 24.3 g (0.131 mole) of potassium phthalimide (Aldrich) and the reaction mixture was heated at reflux under a nitrogen atmosphere for 15 hr. The solvent was evaporated under reduced pressure to heave a viscous, oily residue. The residue was triturated with 200 mL of water and then the mixture was extracted with four 200-mL portions of methylene chloride. The combined methylene chloride extracts were washed with two 200 mL portions of 2N sodium hydroxide solution, twice with 200 mL portions of water and dried over magnesium sulfate. The solvent was evaporated under reduced pressure to give 35.0 g (91%) of title compound as a viscous oil. A sample of this viscous oil was further purified by high pressure liquid chromatography (Waters Associates Prep LC/System 500A, PrepPak ® 500 silica gel; ethyl acetate-hexanes, 1:10). Fractions containing title compound were combined and the solvents were evaporated under reduced pressure to give purified title compound as a colorless, viscous oil.

| Analysis calculated for: | $C_{19}H_{19}NO_2$: C,77.79;H,6.53;N,4.77 |
|---|---|
| | Found: C,77.80;H,6.55;N,4.60 |

PREPARATION 4

5-Butyl-2-imino-4-thiazolidinone hydrate[4:1].

A mixture of 100 g (0.44 mole) of 2-bromohexanoic acid ethyl ester (Aldrich) and 39.0 g (0.51 mole) of thiourea (Baker) in 600 mL of ethanol was stirred and heated on a steam bath for 2 hr. The solvent was evaporated under reduced pressure to leave a solid residue. A 1.0 g sample of this solid was recrystallized from ethanol-water to yield 0.8 g title compound as a white solid, mp 179°–182° C. (lit, mp 183° C., J. Amer. Chem. Soc. 49, 2064 (1927)).

| Analysis calculated for: | $C_7H_{12}N_2OS$: C,48.81;H,7.02;N,16.26 |
|---|---|
| | Found: C,47.95;H,7.04;N,16.10 |
| | Calculated for $C_7H_{12}N_2OS\bullet 0.25H_2O$: C,47.57;H,7.13;N,15.85 |

PREPARATION 5

4-[4-(1,3-Dihydro-1,3-dioxo-2H-isoindol-2-yl)butyl]benzoic acid ethyl ester.

A mixture of 20.7 g (0.086 mole) of 4-(4-chlorobutyl)benzoic acid ethyl ester[1] and 16.0 g (0.0864 mole) of potassium phthalimide (98%, Aldrich) in 150 mL of dimethylformamide was stirred and heated (120° C.) under a nitrogen atmosphere for 12 hr. The solvent was evaporated under reduced pressure and the oily residue was partitioned between water and ethyl acetate (200 mL each). The aqueous layer was further extracted with two 200 mL of ethyl acetate and the combined ethyl acetate layers were washed with 200 mL of water and dried over magnesium sulfate. The solvent was evaporated under reduced pressure to give a brown, viscous oil that solidified upon standing. The solid was purified by chromatography (4.5×90 cm glass column; 520 g of silica gel; ethyl acetate-hexanes, 1:4). Fractions containing title compound were combined and the solvents were evaporated under reduced pressure to yield 13.5 g (45%) of crude title compound as a solid. A sample was recrystallized from ethanol to give white solid, mp 85°–86° C.

| Analysis calculated for: | $C_{21}H_{21}NO_4$: C,71.78;H,6.20;N,3.99 |
|---|---|
| | Found: C,71.83;H,6.02;N,3.99 |

NOTE: [1]The 4-(4-chlorobutyl)benzoic acid ethyl ester was prepared in 47% yield from 4-chlorobutylbenzene (Columbia Organic Chem. Co., Camden, S.C.), oxalylchloride (Eastern Chem. Div., Guardian Chem.

Corp., N.Y.), aluminum chloride and ethanol using the procedure described for the preparation of 4-(3-bromopropyl)benzoic acid ethyl ester.

PREPARATION 6

2-Imino-5-phenyl-4-thiazolidinone.

A mixture of 100 g (0.47 mole) of α-bromophenylacetic acid (Aldrich) and 41.0 g (0.54 mole) of thiourea (Baker) in 600 mL of ethanol was stirred and heated on a steam bath for 4 hr. The solvent was evaporated under reduced pressure to give 142.0 g crude title compound as a white solid. An analytical sample of title compound, mp 249°-252° C., was prepared from 95% ethanol as white flakes.

| Analysis calculated for: | $C_9H_8N_2OS$: C,56.23;H,4.20;N,14.57 |
| --- | --- |
| | Found: C,56.05;H,4.14;N,14.49 |

PREPARATION 7

5-Amino-2-hydroxybenzoic acid methyl ester.

To a stirred solution of 76.6 g (0.5 mole) of 5-aminosalicyclic acid in 252.0 g (8 mole) of methanol was added 150.0 g (1.06 mole) of borontrifluoride etherate (Aldrich) and the mixture was heated at reflux overnight. The reaction mixture was treated with 150 mL of water and filtered. The filtrate pH was adjusted to 8.4 with sodium bicarbonate, and the resulting solid was collected by filtration and air dried to give 43.0 g (51%) of crude title compound as a solid. A sample was dissolved in methylene chloride, treated with charcoal and filtered. The filtrate was concentrated under reduced pressure to give a solid. The solid was recrystallized from methylene chloride-petroleum ether (30°-60° C.) to give title compound as golden-brown needles, mp 95°-98° C.

| Analysis calculated for: | $C_8H_9NO_3$: C,57.48;H,5.43;N,8.38 |
| --- | --- |
| | Found: C,57.28;H,5.40;N,8.35 |

PREPARATION 8

[3-(Dibromomethyl)phenyl]phenylmethanone.

A mixture of 50.0 g (0.255 mole) of 3-methylbenzophenone (Aldrich), 100 g (0.562 mole) of N-bromosuccinimide (Aldrich) and 1.2 g of dibenzoylperoxide in 800 mL of carbon tetrachloride was heated at reflux for 5 hr under flood light illumination. The reaction mixture was filtered through Celite ® and the filtrate was evaporated under reduced pressure to give 102.0 g of a light-yellow solid. An analytical sample, mp 97°-99° C., was prepared from benzene-petroleum ether (30°-60° C.) to give the title compound as an off-white solid.

| Analysis calculated for: | $C_{14}H_{10}Br_2O$: C,47.50;H,2.85 |
| --- | --- |
| | Found: C,47.17;H,2.78 |

PREPARATION 9

3-Benzoylbenzaldehyde.

To a stirred solution of 102 g (0.27 mole) of crude 3-dibromomethylbenzophenone in 700 mL of ethanol and 500 mL of tetrahydrofuran at reflux was added a solution of 84.5 (0.5 mole) of silver nitrate in 120 mL of water and the reaction mixture was stirred and heated at reflux for 2 hr, filtered through Celite ® and the filtrate was evaporated under reduced pressure to leave a semi-solid residue. The solid was partitioned between water and ethyl ether (300 mL each). The layers were separated and the aqueous layer was extracted with 300 mL of ethyl ether. The combined ether extracts were washed with three 200 mL portions of a saturated sodium bicarbonate solution, twice with 200 mL portions of water and dried over magnesium sulfate. The solvent was evaporated under reduced pressure to give 43.0 g of a light-yellow, viscous oil. This oil was a 2:1 mixture of 3-benzoylbenzaldehyde and 3-benzoylbenzoic acid ethyl ester (NMR).

A mixture of this oil and a solution of 70.0 g (0.83 mole) of sodium bicarbonate in 150 mL of water and 1 L of 95% ethanol was stirred and heated at reflux for 30 hr under a nitrogen atmosphere. The reaction mixture was filtered and the filtrate was concentrated to a semi-solid residue. This residue was partitioned between ethyl ether and water (500 mL each). The aqueous layer was extracted with two 300 mL portions of ethyl ether and the combined ether extracts were washed with 400 mL of water and dried over magnesium sulfate. The solvent was evaporated under reduced pressure to give 28.3 g[1] of a golden-brown, viscous oil that solidified upon standing. An analytical sample, mp 59°-62° C., was prepared from benzene-petroleum ether (30°-60° C.) as a light-yellow solid.

| Analysis calculated for: | $C_{14}H_{10}O_2$: C,79.99;H,4.80 |
| --- | --- |
| | Found: C,79.76;H,4.75 |

NOTE: [1]This is a 53% yield based on 3-methylbenzophenone starting material.

PREPARATION 10

4-(3-Chloropropoxy)-3-methoxybenzoic acid methyl ester.

A mixture of 100 g (0.549 mole) of methylvanillate, 172.8 g (1.1 mole) of 1-bromo-3-chloropropane and 228 g (1.65 mole) of anhydrous potassium carbonate in 1 L of acetone was heated at reflux for 20 hr. The mixture was cooled, filtered, and the filtrate concentrated to give a white solid as residue. The solid was triturated with petroleum ether, collected by filtration, and dried to yield 137.8 g (97%) of title compound as a white powder, mp 104°-105° C. (2-propanol).

| Analysis calculated for: | $C_{12}H_{15}ClO_4$: C,55.71;H,5.84 |
| --- | --- |
| | Found: C,55.87;H,5.94 |

PREPARATION 11

4-[3-(1,3-Dihydro-1,3-dioxo-2H-isoindol-2-yl)propoxy]-3-methoxybenzoic acid methyl ester.

A mixture of 66.9 g (0.354 mole) of potassium phthalimide (98%, Aldrich) and 90.0 g (0.348 mole) of 4-(3-chloropropoxy)-3-methyl benzoic acid methyl ester in 450 mL of dimethyl formamide was stirred and heated at reflux for 5 hr then let stir at ambient temperature overnight. The reaction mixture was treated with 3 L of water and the resulting solid was collected by filtration to give 108.5 g (84%) of crude title compound. An 8.0 g sample of this solid was recrystallized from 2-propanol to yield 6.4 g (80%) of title compound as a white solid, mp 127°-128° C.

| Analysis calculated for: | $C_{20}H_{19}NO_6$: C,65.04;H,5.19;N,3.80 |
|---|---|
| | Found: C,64.66;H,5.09;N,3.80 |

PREPARATION 12

4-(3-Chloropropoxy)-3-methoxybenzeneacetic acid ethyl ester.

A mixture of 50 g (0.238 mole of ethyl homovanillate (98% Aldrich), 75 g (0.476 mole) of 1-bromo-3-chloropropane and 98.7 g (0.71 mole) of anhydrous potassium carbonate in 1 L of acetone was heated at reflux for 24 hr. The mixture was filtered and the filtrate was concentrated under reduced pressure to give an oil which gradually crystallized to a semi-solid. The solid was recrystallized from ethyl ether-petroleum ether (30°-60°) to yield 44.4 g (65%) of title compound a white solid, mp 36°-38° C.

| Analysis calculated for: | $C_{14}H_{19}ClO_4$: C,58.64;H,6.68 |
|---|---|
| | Found: C,58.74;H,6.74 |

PREPARATION 13

4-[3-(1,3-Dihydro-1,3-dioxo-2H-isoindol-2-yl)propoxy]-3-methoxybenzeneacetic acid ethyl ester.

A mixture of 40.5 g (0.141 mole) of 4-(3-chloropropoxy)-3-methoxybenzeneacetic acid ethyl ester and 27.2 g (0.144 mole) of potassium phthalimide (98%, Aldrich) in 300 mL of dimethylformamide was stirred and heated at reflux for 5 h, then was stirred at ambient temperature overnight. The solvent was evaporated under reduced pressure to give 52.3 g (93%) of a gummy residue which solidified upon standing. An analytical sample, mp 70°-72° C., was prepared from ethyl ether-petroleum ether (30°-60° C.) as a white solid.

| Analysis calculated for: | $C_{22}H_{23}NO_6$: C,66.49;H,5.83;N,3.52 |
|---|---|
| | Found: C,66.39;H,5.87;N,3.59 |

PREPARATION 14

1,3-Dihydro-1,3-dioxo-2H-isoindol-2-octanoic acid ethyl ester.

A mixture of 26.4 g (0.1 mole) of ethyl-8-bromooctanoate (95%, Pfaltz and Bauer) and 19.6 g (0.1 mole) of potassium phthalimide (98%, Aldrich) in 250 mL of dimethylformamide was stirred and heated at reflux for 4 hr. The solvent was evaporated under reduced pressure and the viscous residue was partitioned between ethyl ether and water (400 mL each). The aqueous layer was further extracted with two 200 mL of ethyl ether. The combined ether extracts were washed with 200 mL of water and dried over magnesium sulfate. The solvent was evaporated under reduced pressure and the viscous, oily residue was triturated with ethyl ether-petroleum ether (30°-60° C.) and the resulting solid was collected by filtration. The filtrate was evaporated under reduced pressure to give 25.2 g (79%) of crude title compound as a viscous oil. A 2.0 g sample of this oil was purified by high pressure liquid chromatography (Waters Associates Prep LC/System 500A; PrepPak ® 500 silica; ethyl acetate-hexanes, 1:20; flow rate: 200 mL/min.). Fractions containing title compound were combined and the solvents were evaporated under reduced pressure to give 1.9 g (95% recovery) of clear liquid.

| Analysis calculated for: | $C_{18}H_{23}NO_4$: C,68.12;H,7.30;N,4.41 |
|---|---|
| | Found: C,68.03;H,7.33;N,4.43 |

PREPARATION 15

1,3-Dihydro-1,3-dioxo-2H-isoindole-2-propanoic acid ethyl ester.

This compound was prepared according to the procedure used to prepare 1,3-dihydro-1,3-dioxo-2H-isoindoleoctanoic acid ethyl ester. Thus, a mixture of 100.0 g (0.55 mole) of 3-bromopropionic acid ethyl ester (99%, Aldrich) and 108.7 g (0.58 mole) of potassium phthalimide (98%, Aldrich) in 300 mL of dimethylformamide gave 59.4 g (44%) of crude title compound as an oily residue. A 3.0 g sample of this oil was purified by high-pressure liquid chromatography (Waters Associates Prep LC/System 500A; PrepPak ® 500 silica; ethyl acetate-hexanes, 1:10). Fractions containing title compound were combined and the solvents evaporated under reduced pressure to give 2.3 g (77% recovery) of a pale-yellow oil.

| Analysis calculated for: | $C_{13}H_{13}NO_4$: C,63.15;H,5.30;N,5.66 |
|---|---|
| | Found: C,62.90;H,5.32;N,5.49 |

PREPARATION 16

1,3-Dihydro-1,3-dioxo-2H-isoindole-2-hexanoic acid ethyl ester.

This compound was prepared according to the procedure used to prepare 1,3-dihydro-1,3-dioxo-2H-isoindoleoctanoic acid ethyl ester. Thus, a mixture of 62.3 g (0.265 mole) of 6-bromohexanoic acid ethyl ester (ethyl 6-bromocapronate, 95%, Fluka) and 52.4 g (0.277 mole) of potassium phthalimide (98%, Aldrich) in 200 mL of dimethylformamide gave 67 g (87%) of crude title compound as a viscous oil. A 2.0 g sample of this oil was purified by high-pressure liquid chromatography (Waters Associates Prep LC/System 500A; PrepPak ® 500 silica; ethyl acetate-hexanes, 1:10; flow rate 200 mL/min). Fractions containing title compound were combined and the solvents evaporated under reduced pressure to give 1.9 g (95% recovery) of colorless liquid.

| Analysis calculated for: | $C_{16}H_{19}NO_4$: C,66.42;H,6.62;N,4.84 |
|---|---|
| | Found: C,66.20;H,6.64;N,4.84 |

PREPARATION 17

1,3-Dihydro-1,3-dioxo-2H-isoindole-2-pentanoic acid ethyl ester.

This compound was prepared according to the procedure used to prepare 1,3-dihydro-1,3-dioxo-2H-isoindole octanoic acid ethyl ester. Thus, a mixture of 100 g (0.48 mole) of ethyl 5-bromovalerate (99%, Aldrich) and 94.5 g (0.50 mole) of potassium phthalimide (98%, Aldrich) in 300 mL of dimethylformamide gave 107.6 g (81%) of viscous oil. A 2.0 g sample of this oil was purified by high-pressure liquid chromatography (Waters Associates Prep LC/System 500A; PrepPak ® 500 silica; ethyl acetate-hexanes, 1:10). Fractions containing title compound were combined and the solvents evaporated under reduced pressure to give 1.9 g (95% recovery) of colorless liquid.

| Analysis calculated for: | $C_{15}H_{17}NO_4$: C,65.44;H,6.22;N,5.09 |
| --- | --- |
| | Found: C,65.33;H,6.27;N,5.09 |

PREPARATION 18

2-Mercaptohexanoic acid.

A mixture of 100 g (0.44 mole) of 2-bromohexanoic acid ethyl ester (Aldrich) and 39.0 g (0.51 mole) of thiourea (Fisher) in 600 mL of ethanol was stirred and heated on a steam bath for 2 hr. The solvent was evaporated under reduced pressure to give a solid residue. The solid was treated with 75 g (0.44 mole) of barium hydroxide in 1 L of 20% aqueous ethanol and the reaction mixture was stirred and heated at reflux for 20 hr. An additional 30.0 g (0.18 mole) of barium hydroxide was added and stirring and heating was continued for 20 hr. The reaction mixture was filtered and the filtrate pH was adjusted to 2 with concentrated hydrochloric acid. The mixture was extracted with three 500 mL portions of ethyl ether. The ethereal extracts were washed twice with 300 mL portions of water and dried over magnesium sulfate. The solvent was evaporated under reduced pressure to yield 52.8 g (80%) of 2-mercaptohexanoic acid as a light-yellow, viscous oil that has a sharp onion smell.

PREPARATION 19

α-Mercaptophenylacetic acid.

Hydrolysis of 142 g of 5-phenyl-2-imino-4-thiazolidinone with barium hydroxide in 20% aqueous ethanol gave 55 g of α-mercaptophenylacetic acid (70% yield).

PREPARATION 20

4-(3-Aminopropoxy)benzoic acid ethyl ester.

A stirred mixture of 11.8 g (0.033 mole) of 4-[3-(1,3-dihydro-1,3-dioxo-2H-isoindol-2-yl)propoxy]benzoic acid ethyl ester and 2.4 g of 85% hydrazine hydrate in 300 mL of ethanol was heated at reflux temperature for 3 hr. After cooling the reaction mixture was filtered and the filtrate was concentrated under reduced pressure. The residue was treated with 450 mL of 2N hydrochloric acid and filtered. The filtrate was basified to pH 11 with potassium carbonate and the mixture was extracted twice with 200 mL portions of methylene chloride. The combined extract was washed with 200 mL of water and the solvent was evaporated under reduced pressure to give 3.8 g of oil that solidified on standing.

PREPARATION 21

4-(Aminomethyl)phenol monohydrobromide.

A mixture of 40.0 g (0.29 mole) of 4-methoxybenzylamine (98%, Aldrich) and 150 mL of 48% hydrobromic acid (Baker) was stirred and heated at reflux for 18 hr, then stirred at ambient temperature for 72 hr. The precipitate was collected by filtration, washed with ethyl ether (300 mL) and dried to give 21.0 g (35%) of the title compound as an off-white solid, mp 215°–217° C.

| Analysis calculated for: | $C_7H_6NO \cdot HBr$: C,41.20;H,4.94;N,6.86 |
| --- | --- |
| | Found: C,41.17;H,5.28;N,6.61 |

PREPARATION 22

2-(6-Phenylhexyl)-1,3-dihydro-1,3-dioxo-2H-isoindole.

This compound was prepared by the procedure used in Preparation 3. Thus, a solution of 15.0 g (0.077 mole) of 6-phenyl-1-hexylchloride (Fairfield Chemical Co.) and 14.4 g (0.076 mole) of potassium phthalimide (98%, Aldrich) in 120 mL of dimethylformamide gave 23.7 g of a viscous oil that solidified upon standing. The solid was purified by high pressure liquid chromatography (Waters Associates Prep LC/System 500A; PrepPak ® 500/silica; ethyl acetate-hexanes, 1:10; flow rate 150 mL/min). Fractions containing the desired product were combined and the solvents evaporated under reduced pressure to give 17.8 g (76%) of viscous oil that solidified upon standing. A sample of the solid was recrystallized from ethyl acetate-petroleum ether (30°–60° C.) to yield a white solid, mp 54°–57° C.

| Analysis calculated for: | $C_{20}H_{21}NO_2$: C,78.15;H,6.89;N,4.56 |
| --- | --- |
| | Found: C,78.00;H,6.98;N,4.55 |

PREPARATION 23

4-(3-Bromopropyl)benzoic acid ethyl ester.

To a cold (ice bath) stirred solution of 50.0 g (0.25 mole) of 1-bromo-3-phenylpropane (Aldrich) and 31.9 g (0.25 mole) of oxalyl chloride in 300 mL of trichloroethylene was added, portionwise, 33.3 g (0.25 mole) of aluminum chloride. The reaction mixture was stirred for 0.5 hr and then poured into ice water. The layers were separated and the aqueous layer was extracted with three 100 mL portions of methylene chloride. The combined organic layers were washed twice with 200 mL portions of water and dried (magnesium sulfate). The solvents were evaporated under reduced pressure to leave 63.6 g (97%) of 4-(3-bromopropyl)benzoyl chloride as an oil. To a solution of the acid chloride in 120 mL of dry benzene was added 60 mL of absolute ethanol and the mixture was heated at reflux for 3 hr. The solvents were evaporated under reduced pressure to give 63.4 g (93.5%) of an oil. The oil was purified by chromatography (3.5×90 cm glass column, 200 g of silica gel, benzene-hexane, 1:1). Fractions containing the desired component were combined and the solvents evaporated under reduced pressure to give 60.6 g (89%) of the title compound as a pale yellow oil.

| Analysis calculated for: | $C_{12}H_{15}BrO_2$: C,53.16;H,5.58 |
| --- | --- |
| | Found: C,53.08;H,5.58 |

EXAMPLE 1

5-Butyl-2-(3-phenoxyphenyl)-3-(4-phenylbutyl)-4-thiazolidinone cis/trans (1:3) isomers.

A mixture of 7.8 g (0.039 mole) of 3-phenoxybenzaldehyde (Fluka), 6.8 g (0.046 mole) of 2-mercaptohexanoic acid and 6.7 g (0.045 mole) of 4-phenylbutylamine (98%, Aldrich) in 250 ml of benzene was stirred and heated at reflux overnight utilizing a Dean-Stark trap. The reaction mixture was poured into a solution of 400 ml of water and 20 ml of concentrated ammonium hydroxide. The layers were separated and the organic layer was washed with 200 ml of 2N hydrochloric acid, 200 ml of water and dried (magnesium sulfate). The solvent was evaporated under reduced pressure to give 17.8 g of a light yellow, viscous oil. The oil was purified by high pressure liquid chromatography (Waters Associates Prep LC/System 500A; PrepPak 500 ® silica gel; ethyl acetate-hexanes, 1:10). Fractions containing the product were combined and the solvents were evaporated under reduced pressure to yield 5.7 g (31%) of the title compound as an orange, viscous oil which was determined to be a 75:25 mixture of trans:cis isomers ($^{13}$C NMR).

| Analysis calculated for: | $C_{29}H_{33}NO_2S$: C,75.78;H,7.24;N,3.05 |
|---|---|
| | Found: C,75.39;H,7.20;N,3.02 |

EXAMPLE 2

5-Butyl-3-(4-hydroxyphenyl)-2-(3-phenoxyphenyl)-4-thiazolidinone, cis/trans (1:3) isomers.

Using the procedure of Example 1, a mixture of 5.0 g (0.025 mole) of 3-phenoxybenzaldehyde (Fluka), 3.7 g (0.025 mole) of 2-mercaptohexanoic acid and 2.8 g (0.025 mole) of 4-aminophenol in 150 ml of benzene gave 9.2 g of crude solid product after overnight reflux. Recrystallization twice from ethyl acetate-hexanes gave 4.1 g (39%) of the title compound as a white solid, mp 151°–153° C. which is a 1:3 mixture of cis:trans isomers as determined by $^{13}$C NMR.

| Analysis calculated for: | $C_{25}H_{25}NO_3S$: C,71.57;H,6.01;N,3.34 |
|---|---|
| | Found: C,71.57;H,5.99;N,3.19 |

EXAMPLE 3

5-Butyl-3-(4-hydroxyphenyl)-2-(3-phenoxyphenyl)-4-thiazolidinone cis isomer.

This compound was isolated from the mother liquor of Example 2 in 12% yield by chromatography on silica gel (4.5×110 cm glass column, 500 g) with ethyl acetate:hexanes (1:2) as a pure isomer. The solid was recrystallized from ethyl acetate-petroleum ether (30°–60° C.) to give a white solid, mp 141°–143° C. Rf (ethyl acetate-hexanes, 1:2, silica): 0.24.

| Analysis calculated for: | $C_{25}H_{25}NO_3S$: C,71.57;H,6.01;N,3.34 |
|---|---|
| | Found: C,71.84;H,5.99;N,3.30 |

EXAMPLE 4

5-Butyl-3-(4-hydroxyphenyl)-2-(3-phenoxyphenyl)-4-thiazolidinone trans isomer.

This compound was isolated from the mother liquor of Example 2 in 15% yield by chromatography (500 g of silica gel, 4.5×110 cm glass column) with ethyl acetate:hexanes (1:2) as a pure isomer. The solid was recrystallized from ethyl acetate-petroleum ether (30°–60° C.) to give a white solid, mp 159°–161° C. Rf (ethyl acetate-hexanes, 1:2, silica): 0.18.

| Analysis calculated for: | $C_{25}H_{25}NO_3S$: C,71.57;H,6.01;N,3.34 |
|---|---|
| | Found: C,71.88;H,6.12;N,3.39 |

EXAMPLE 5

4-[4-[5-Butyl-4-oxo-2-(3-phenoxyphenyl)-3-thiazolidinyl]butyl]benzoic acid ethyl ester trans isomer.

A mixture of 12.0 g (0.034 mole) of 4-[4-(1,3-dihydro-1,3-dioxo-2H-isoindo-2-yl)butyl]benzoic acid ethyl ester and 2.5 g of 85% hydrazine hydrate in 250 ml of ethanol was stirred and heated at reflux for 4 hr. The resulting solid was removed by filtration. The filtrate was concentrated under reduced pressure and the semi-solid residue was stirred with 100 ml of 10% sodium hydroxide solution for 2 hr. The reaction mixture was extracted with four 150 ml portions of methylene chloride and the extracts were washed twice with 100 ml portions of water and dried (magnesium sulfate). The solvent was evaporated under reduced pressure and the semi-solid residue was triturated with 200 ml of ethyl ether and filtered. The filtrate was concentrated under reduced pressure to yield 3.2 g (42%) of 4-(4-aminobutyl)benzoic acid ethyl ester as a brown oil which was used without further purification in the next synthetic step.

A solution of 2.9 g (0.015 mole) of 3-phenoxybenzaldehyde (Fluka), 2.1 g (0.015 mole) of 2-mercaptohexanoic acid and 3.2 g (0.0145 mole) of 4-(4-aminobutyl)benzoic acid ethyl ester in 250 ml of benzene was stirred and heated at reflux over the weekend utilizing a Dean-Stark trap. The reaction mixture was poured into a solution of 400 ml of water and 15 ml of concentrated ammonium hydroxide. The layers were separated and the organic layer was washed with two 100-ml portions of water and dried (magnesium sulfate). The solvent was evaporated under reduced pressure to give 7.5 g of a yellow, viscous oil. The oil was purified by chromatography (4.5×110 cm glass column; 550 g of silica gel; ethyl acetate-hexanes, 1:10). Fractions containing the pure product were combined and the solvents were evaporated under reduced pressure to give 0.8 g of the title compound as a light yellow gum; Rf (ethyl acetate-hexanes, 1:10, silica): 0.15.

| Analysis calculated for: | $C_{32}H_{37}NO_4S$: C,72.29;H,7.01;N,2.63 |
|---|---|
| | Found: C,72.19;H,7.04;N,2.75 |

EXAMPLE 6

4-[4-[5-Butyl-4-oxo-2-(3-phenoxyphenyl)-3-thiazolidinyl]butyl]benzoic acid ethyl ester cis isomer.

This compound was isolated (chromatography) in 19% yield as a pale-yellow gum in the preparation of 4-[4-[5-butyl-4-oxo-2-(3-phenoxyphenyl)-3-thiazolidinyl]butyl]benzoic acid ethyl ester trans isomer; Rf (ethyl acetate-hexanes, 1:10; silica): 0.19.

| Analysis calculated for: | $C_{32}H_{37}NO_4S$: C, 72.29; H, 7.01; N, 2.63 |
|---|---|
| | Found: C, 72.46; H, 7.06; N, 2.54 |

EXAMPLE 7

5-Methyl-2-(3-phenoxyphenyl)-3-(4-phenylbutyl)-4-thiazolidinone cis/trans (2:3) isomers.

Using the procedure of Example 1, 7.8 g (0.039 mole) of 3-phenoxybenzaldehyde (Fluka), 4.2 g (0.04 mole) of 2-mercaptopropionic acid (Aldrich) and 6.0 g (0.039 mole) of 4-phenylbutylamine (98% Alrich) in 300 ml of benzene and overnight reflux yielded 16.4 g of a light yellow viscous oil that was purified by high pressure liquid chromatography (Waters Associates Prep LC/System 500A; PrepPak ® 500 silica; ethyl acetate-hexanes, 1:10) to obtain 14.6 g (88%) of light yellow, viscous oil which was determined by $^{13}C$ NMR to be a 2:3 mixture of cis/trans isomers.

| Analysis calculated for: | $C_{26}H_{27}NO_2S$; C, 74.79; H, 6.52; N, 3.35 |
|---|---|
| | Found: C, 74.58; H, 6.47; N, 3.34 |

EXAMPLE 8

2-(3-Benzoylphenyl)-5-butyl-3-(4-phenylbutyl)-4-thiazolidinone cis/trans (2:3) isomers.

Using the procedure of Example 1 and purifying by chromatography (4.5×100 cm glass column; 550 silica; ethyl acetate:hexanes 1:10) the title isomer mixture was obtained as a gum in 64% yield (3.7 g) from 2.6 g (0.0124 mole) of 3-benzoylbenzaldehyde, 1.8 g (0.0124 mole) of 2-mercaptohexanoic acid and 1.9 g (0.0124 mole) of 4-phenylbutylamine (98%, Aldrich).

| Analysis calculated for: | $C_{30}H_{33}NO_2S$: C, 76.40; H, 7.05; N, 2.97 |
|---|---|
| | Found: C, 76.17; H, 7.06; N, 2.96 |

EXAMPLE 9

2-(3-Phenoxyphenyl)-5-phenyl-3-(4-phenylbutyl)-4-thiazolidinone cis isomer.

Using the procedure and purification of Example 5, the title compound was obtained in 25% yield (3.1 g) as an orange gum from 5.0 g (0.0252 mole) of 3-phenoxybenzaldehyde (Fluka), 4.2 g (0.0252 mole) of α-mercaptophenylacetic acid, and 3.8 (0.0252 mole) of 4-phenylbutylamine (98%, Aldrich) after refluxing in 250 ml of benzene for 36 hr. Rf (ethyl acetate-hexanes 1:10; silica gel): 0.25.

| Analysis calculated for: | $C_{31}H_{29}NO_2S$: C, 77.63; H, 6.09; N, 2.92 |
|---|---|
| | Found: C, 78.01; H, 6.20; N, 2.96 |

EXAMPLE 10

2-(3-Phenoxyphenyl)-5-phenyl-3-(4-phenylbutyl)-4-thiazolidinone trans isomer.

This isomer was isolated in the chromatographic procedure of Example 9 in 22% yield as an orange gum. Rf (ethyl acetate-hexanes 1:10; silica gel): 0.18.

| Analysis calculated for: | $C_{31}H_{29}NO_2S$: C, 77.63; H, 6.09; N, 2.92 |
|---|---|
| | Found: C, 77.57; H, 6.04; N, 2.92 |

EXAMPLE 11

5,5-Dimethyl-2-(3-phenoxyphenyl)-3-(4-phenylbutyl)-4-thiazolidinone.

Using the procedures of Example 5, the title compound was prepared as a light yellow viscous oil (8.4 g, 65%) from 5.9 g (0.030 mole) of 3-phenoxybenzaldehyde (Fluka), 3.6 g (0.030 mole) of 2-mercapto-2-methylpropionic acid, and 4.6 g (0.030 mole) of 4-phenylbutylamine after refluxing in 250 ml of benzene overnight.

| Analysis calculated for: | $C_{27}H_{29}NO_2S$: C, 75.14; H, 6.77; N, 3.25 |
|---|---|
| | Found: C, 75.41; H, 6.84; N, 3.25 |

EXAMPLE 12

5-(1-Methylethyl)-2-(3-phenoxyphenyl)-3-(4-phenylbutyl)-4-thiazolidinone cis/trans (1:1) isomers.

Using the procedures of Example 5 the title isomer mixture is obtained (6.9 g, 51%) as a yellow gum from 5.9 g (0.030 mole) of 3-phenoxybenzaldehyde (Fluka), 5.0 (0.037 mole) of 2-mercapto-3-methylbutyric acid and 4.6 g (0.030 mole) of 4-phenylbutylamine (98%, Aldrich) after refluxing with 250 ml of benzene overnight.

| Analysis calculated for: | $C_{28}H_{31}NO_2S$: C, 75.47; H, 7.01; N, 3.14 |
|---|---|
| | Found: C, 75.55; H, 7.05; N, 3.16 |

EXAMPLE 13

3-(4-Hydroxyphenyl)-2-(3-phenoxyphenyl)-5-phenyl-4-thiazolidinone cis/trans (3:17) isomers.

A mixture of 5.9 g (0.030 mole) of 3-phenoxybenzaldehyde (Fluka), 5.0 g (0.030 mole) of α-mercaptophenylacetic acid and 3.3 g (0.030 mole) of 4-aminophenol (Matheson, Coleman & Bell) in 250 ml of benzene was stirred and heated at reflux for 36 hr utilizing a Dean-Stark trap. The reaction mixture was filtered through Celite ® and the filtrate was poured into a solution of 400 ml of water and 18 ml of concentrated ammonium hydroxide. The layers were separated and the organic layer was washed twice with 200 ml portions of 2N hydrochloric acid, 200 ml of water and dried (magnesium sulfate). The solvent was evaporated under reduced pressure and the viscous, oily residue was purified by chromatography (4.5×110 cm glass column; 550 g of silica gel; ethyl acetate-hexanes, 1:2). Fractions containing the product were combined and the solvents were evaporated under reduced pressure to give 3.2 g (24%) of solid. The solid was dissolved in 70 ml of ethyl acetate, treated with charcoal and filtered. The filtrate was evaporated under reduced pressure and the solid residue was recrystallized from ethyl acetate-petroleum ether (30°-60° C.) to give 3.0 g (23%) of the title compound as an off-white solid (mp 203°-207° C.) which is a (15:85) mixture of cis-trans isomers ($^{13}C$ NMR).

| Analysis calculated for: | $C_{27}H_{21}NO_3S$: C, 73.78; H, 4.82; N, 3.19 |
|---|---|
| | Found: C, 73.53; H, 4.81; N, 3.16 |

EXAMPLE 14

5-Butyl-2-(3-phenoxyphenyl)-3-(3-phenylpropyl)-4-thiazolidinone cis isomer.

This pure isomer was isolated in the chromatographic procedures of Example 15 (2.4 g, 21%) as a yellow viscous oil. Rf (ethyl acetate-hexanes, 1:10; silica): 0.27.

| Analysis calculated for: | $C_{28}H_{31}NO_2S$: C, 75.47; H, 7.01; N, 3.14 |
|---|---|
| | Found: C, 75.21; H, 7.03; N, 3.14 |

EXAMPLE 15

5-Butyl-2-(3-phenoxyphenyl)-3-(3-phenylpropyl)-4-thiazolidinone cis/trans (17:83) isomers.

Using the procedures of Example 5, the title isomer mixture is obtained (6.4 g, 55%) as a viscous yellow oil from 5.2 g (0.026 mole) of 3-phenoxybenzaldehyde (Fluka), 3.6 g (0.026 mole) of 3-phenylpropylamine (98%, Aldrich) and 3.9 g (0.026 mole) of 2-mercaptohexanoic acid after overnight reflux in 250 ml of benzene.

| Analysis calculated for: | $C_{28}H_{31}NO_2S$: C, 75.47; H, 7.01; N, 3.14 |
|---|---|
| | Found: C, 75.34; H, 7.04; N, 3.15 |

EXAMPLE 16

5-Butyl-2-(3-phenoxyphenyl)-3-(3-phenylpropyl)-4-thiazolidinone trans isomers.

This compound was isolated in the chromatographic procedures of Example 15 (1.2 g, 10%) as a yellow viscous oil. Rf (ethyl acetate-hexanes, 1:10, silica): 0.22.

| Analysis calculated for: | $C_{28}H_{31}NO_2S$: C, 75.47; H, 7.01; N, 3.14 |
|---|---|
| | Found: C, 75.37; H, 7.02; N, 3.12 |

EXAMPLE 17

5-Butyl-2-(3-phenoxyphenyl)-3-(2-phenylethyl)-4-thiazolidinone cis/trans (2:3) isomers.

Using the procedures used in Example 5, the title isomer mixture was obtained (9.2 g, 81%) as a yellow viscous oil from 5.2 g (0.026 mole) of 3-phenoxybenzaldehyde, 3.2 g (0.026 mole) of 2-phenylethylamine (Aldrich) and 3.9 g (0.026 mole) of 2-mercaptohexanoic acid after overnight reflux in 250 ml of benzene.

| Analysis calculated for: | $C_{27}H_{29}NO_2S$: C, 75.14; H, 6.77; N, 3.25 |
|---|---|
| | Found: C, 74.99; H, 6.76; N, 3.23 |

EXAMPLE 18

5-Butyl-2-(3-phenoxyphenyl)-3-[2-(2-pyridinyl)ethyl]-4-thiazolidinone cis/trans (1:3) isomers.

A solution of 7.9 g (0.04 mole) of 3-phenoxybenzaldehyde (Fluka) and 4.9 g (0.04 mole) of 2-(2-aminoethyl)pyridine (Aldrich) in 250 ml of benzene was stirred and heated at reflux for 1 hr utilizing a Dean-Stark trap. To this reaction mixture was added 5.9 g (0.04 mole) of 2-mercaptohexanoic acid and the stirred reaction mixture was heated at reflux overnight utilizing a Dean-Stark trap. The reaction mixture was poured into a solution of 400 ml of water and 20 ml of concentrated ammonium hydroxide. The layers were separated and the organic layer was washed thrice with 200 ml portions of 2N hydrochloric acid, once with 200 ml of water and dried (magnesium sulfate). The solvent was evaporated under reduced pressure and the gummy residue was purified by chromatography (4.5×110 cm glass column; 520 g of silica; benzene-triethylamine, 100:4). Fractions containing the product were combined and the solvents evaporated under reduced pressure to give 10.5 g (61%) of the title compound as an orange, viscous oil which is a (1:3) cis-trans mixture ($^{13}$C NMR).

| Analysis calculated for: | $C_{26}H_{28}N_2O_2S$: C, 72.19; H, 6.52; N, 6.48 |
|---|---|
| | Found: C, 71.93; H, 6.54; N, 6.56 |

EXAMPLE 19

5-Butyl-2-(3-phenoxyphenyl)-3-(phenylmethyl)-4-thiazolidinone cis/trans (1:1) isomers.

Using the reaction procedure and chromatographic procedure of Example 1, the title isomer mixture was obtained (8.3 g, 76%) as a light yellow viscous oil from a mixture of 5.2 g (0.026 mole) of 3-phenoxybenzaldehyde (Fluka), 2.8 g (0.026 mole) of benzylamine, and 3.9 g (0.026 mole) of 2-mercaptohexanoic acid after refluxing for 8 hr in 250 ml benzene.

| Analysis calculated for: | $C_{26}H_{27}NO_2S$: C, 74.79; H, 6.52; N, 3.35 |
|---|---|
| | Found: C, 74.57; H, 6.49; N, 3.41 |

EXAMPLE 20

5-[5-Butyl-4-oxo-2-(3-phenoxyphenyl)-3-thiazolidinyl]-2-hydroxybenzoic acid methyl ester trans isomer.

Using the procedures of Example 1, the title compound was obtained (5.2 g, 22%) as a white solid [mp 120°–122° C. (ethyl acetate-petroleum ether)] from a mixture of 9.9 g (0.05 mole) of 3-phenoxybenzaldehyde, 8.4 g (0.050 mole) of 5-amino-2-hydroxybenzoic acid methyl ester and 7.4 g (0.05 mole) of 2-mercaptohexanoic acid after refluxing overnight in 350 ml of benzene. Rf (ethyl acetate-hexanes, 1:10; silica gel): 0.10. (Also obtained was 5.3 g (22%) of a mixture of cis-trans isomers.)

| Analysis calculated for: | $C_{27}H_{27}NO_5S$: C, 67.91; H, 5.70; N, 2.93 |
|---|---|
| | Found: C, 67.97; H, 5.70; N, 2.93 |

EXAMPLE 21

2-(3-Benzoylphenyl)-5-butyl-3-(4-hydroxyphenyl)-4-thiazolidinone cis isomer.

This compound was isolated in 24% (1.6 g) yield as a pure cis isomer (solid) during the chromatographic purification of Example 22. The solid was dissolved in ethyl acetate, treated with charcoal and filtered. The filtrate was concentrated and the solid residue was recrystallized from ethyl acetate-petroleum ether (30°–60° C.) to give the cis isomer as an off-white solid, mp 151°–153° C. Rf (ethyl acetate-hexanes, 1:2; silica): 0.21.

| Analysis calculated for: | $C_{26}H_{25}NO_3S$: C, 72.36; H, 5.84; N, 3.25 |
|---|---|
| | Found: C, 72.29; H, 5.83; N, 3.22 |

EXAMPLE 22

2-(3-Benzoylphenyl)-5-butyl-3-(4-hydroxyphenyl)-4-thiazolidinone trans isomer.

A mixture of 3.3 g (0.0157 mole) of 3-benzoylbenzaldehyde and 1.7 g (0.0157 mole) of 4-aminophenol in 250 ml of benzene was stirred and heated at reflux for 4 hr. utilizing a Dean-Stark trap. To this mixture was added 2.4 g (0.0157 mole) of 2-mercaptohexanoic acid and the mixture was heated at reflux for 40 hr. The mixture was poured into a solution of 400 ml of water and 20 ml of concentrated ammonium hydroxide. The layers were separated and the organic layer was washed with 200 ml of water and dried (magnesium sulfate). The solvent was evaporated under reduced pressure and the brown, gummy residue was purified by chromatography (4.5×110 cm glass column; 550 g of silica gel; ethyl acetate-hexanes, 1:2). Fractions containing the trans isomer were combined and the solvents were evaporated under reduced pressure to give 3.6 g of a gummy residue that solidified upon standing. The solid was dissolved in ethyl acetate, treated with charcoal and filtered. The filtrate was concentrated to a solid. The solid was recrystallized from ethyl acetate-petroleum ether (30°–60° C.) to give 3.3 g (49%) of the title compound as a white solid, mp 134°–135° C. Rf (ethyl acetate-hexanes, 1:2, silica): 0.14.

| Analysis calculated for: | $C_{26}H_{25}NO_3S$: C, 72.36; H, 5.84; N, 3.25 |
|---|---|
| | Found: C, 71.93; H, 5.84; N, 3.19 |

EXAMPLE 23

5-[5-Butyl-4-oxo-2-(3-phenoxyphenyl)-3-thiazolidinyl]-2-hydroxybenzoic acid trans isomer.

To a stirred mixture of 4.1 g (0.0086 mole) of 5-[5-butyl-4-oxo-2-(3-phenoxyphenyl)-3-thiazolidinyl]-2-hydroxybenzoic acid methyl ester, trans isomer in 500 ml of 95% ethanol was added a solution of 10.0 g (0.119 mole) of sodium bicarbonate in 100 ml of water and the reaction mixture was stirred and heated at reflux for 4 hr under a nitrogen atmosphere. The reaction mixture was filtered and the filtrate was concentrated to 50 ml under reduced pressure. This concentrate was treated with 200 ml of water and the solution pH was adjusted to 1.5 with concentrated hydrochloric acid. The white solid that precipitated was collected by filtration, washed with 200 ml of water and air dried to give 3.9 g (98%) of a white solid. The solid was recrystallized from isopropyl ether-petroleum ether (30°–60° C.) to give 3.1 g (79%) of the title compound as an off-white solid, mp 154°–156° C.

| Analysis calculated for: | $C_{26}H_{25}NO_5S$: C, 67.37; H, 5.44; N, 3.02 |
|---|---|
| | Found: C, 67.47; H, 5.62; N, 2.97 |

EXAMPLE 24

4-[5-Butyl-4-oxo-2-(3-phenoxyphenyl)-3-thiazolidinyl]benzoic acid ethyl ester cis isomer.

This compound was isolated (chromatography) in 19% (2.7 g) yield as a pure cis isomer (solid) in the preparation of the compound of example 25. The solid was recrystallized from ethyl acetate-petroleum ether (30°–60° C.) to give the title compound as an off-white solid, mp 102°–105° C. Rf (ethyl acetate-hexanes, 1:10; silica): 0.2.

| Analysis calculated for: | $C_{28}H_{29}NO_4S$: C, 70.71; H, 6.15; N, 2.95 |
|---|---|
| | Found: C, 70.84; H, 6.16; N, 2.96 |

EXAMPLE 25

4-[5-Butyl-4-oxo-2-(3-phenoxyphenyl)-3-thiazolidinyl]benzoic acid ethyl ester trans isomer.

Following the procedures used in Example 5, the title compound was prepared (3.0 g, 21%) as a white solid (mp 113°–115° C.) (after dissolving in ethyl acetate, treating with charcoal, filtering, concentrating and the recrystallization from ethyl acetate-petroleum ether) from 5.9 g (0.030 mole) of 3-phenoxybenzaldehyde (Fluka), 4.4 g (0.030 mole) of 2-mercaptohexanoic acid and 5.0 g (0.030 mole) of 4-aminobenzoic acid ethyl ester after heating overnight at reflux in 250 ml of benzene.

| Analysis calculated for: | $C_{28}H_{29}NO_4S$: C, 70.71; H, 6.15; N, 2.95 |
|---|---|
| | Found: C, 70.99; H, 6.17; N, 2.97 |

EXAMPLE 26

5-[2-(3-Benzoylphenyl)-5-butyl-4-oxo-3-thiazolidinyl]-2-hydroxybenzoic acid methyl ester cis isomer.

This compound was isolated (chromatography) in 7% yield (1.8 g) as a pure cis isomer (orange glass) in the preparation of the compound of Example 27. Rf (ethyl acetate-hexanes, 1:4; silica): 0.24.

| Analysis calculated for: | $C_{28}H_{27}NO_5S$: C, 68.69; H, 5.56; N, 2.86 |
|---|---|
| | Found: C, 68.91; H, 5.55; N, 2.81 |

EXAMPLE 27

5-[2-(3-Benzoylphenyl)-5-butyl-4-oxo-3-thiazolidinyl]-2-hydroxybenzoic acid methyl ester cis/trans isomers.

A mixture of 10.5 g (0.05 mole) of 3-benzoylbenzaldehyde and 8.4 g (0.05 mole), of 5-amino-2-hydroxybenzoic acid methyl ester in 500 ml of benzene was stirred and heated at reflux for 2 hr utilizing a Dean-Stark trap. To this mixture was added 7.4 g (0.05 mole) of 2-mercaptohexanoic acid and the mixture was stirred and heated at reflux overnight. The reaction mixture was poured into a solution of 600 ml of water and 25 ml of concentrated ammonium hydroxide. The layers were separated and the organic layer was washed twice with 300 ml of water, dried (magnesium sulfate), and the solvent was evaporated under reduced pressure to give a dark, viscous, oily residue. The residue was partitioned between 300 ml of ethyl ether and 150 ml of 6N hydrochloric acid. The layers were separated and the organic layer was washed twice with 150 ml portions of 6N hydrochloric acid, twice with 200 ml portions of water and dried (magnesium sulfate). The solvent was evaporated under reduced pressure to give 14.9 g of a golden-brown viscous oil. The oil was purified by chromatography (4.5×110 cm glass column; 550 g of silica gel; ethyl acetate-hexanes, 1:4). Fractions containing the product were combined, the solvents evaporated under reduced pressure and the residue (5.5 g) was dissolved in methylene chloride, treated with charcoal and filtered through a 50 g layer of silica gel. The filtrate was evaporated under reduced pressure to give 4.9 g (20%) of the title compound as an orange glass which is a (4:96) cis-trans isomeric mixture ($^{13}C$ NMR).

| Analysis calculated for: | $C_{28}H_{27}NO_5S$; C, 68.69; H, 5.56; N, 2.86 |
| --- | --- |
| | Found: C, 68.84; H, 5.61; N, 2.86 |

EXAMPLE 28

4-[5-Butyl-4-oxo-2-(3-phenoxyphenyl)-3-thiazolidinyl]benzoic acid cis/trans isomers.

To a stirred mixture of 2.5 g (0.0053 mole) of 4-[5-butyl-4-oxo-2-(3-phenoxyphenyl)-3-thiazolidinyl]benzoic acid ethyl ester, cis isomer in 500 ml of 95% ethanol was added a solution of 5.5 g (0.066 mole) of sodium bicarbonate in 100 ml of water and the reaction mixture was stirred and heated at reflux for 16 hr under a nitrogen atmosphere. The reaction mixture was filtered and the filtrate was evaporated under reduced pressure to give a semi-solid residue. The residue was partitioned between water and ethyl ether (200 ml each). The layers were separated and the aqueous layer pH was adjusted to 2 with concentrated hydrochloric acid. The mixture was extracted with three 200 ml portions of ethyl ether. The ether extracts were washed with 200 ml of water, dried (magnesium sulfate) and the solvent was evaporated under reduced pressure to give 1.9 g (79%) of a semi-solid residue. The solid was recrystallized from ethyl ether-petroleum ether (30°-60° C.) to give 1.6 g (67%) of the title compound as a white solid, mp 130°-134° C., as a (35:65) cis-trans isomeric mixture ($^{13}C$ NMR).

| Analysis calculated for: | $C_{26}H_{25}NO_4S$: C, 69.78; H, 5.63; N, 3.13 |
| --- | --- |
| | Found: C, 69.78; H, 5.63; N, 3.18 |

EXAMPLE 29

4-[3-[5-Butyl-4-oxo-2-(3-phenoxyphenyl)-3-thiazolidinyl]propoxy]benzoic acid ethyl ester cis-trans isomers.

A solution of 9.9 g (0.05 mole) of 3-phenoxybenzaldehyde (Fluka) and 11.2 g (0.05 mole) of 4-(3-aminopropoxy)benzoic acid ethyl ester in 250 ml of benzene was stirred and heated at reflux for 2 hr utilizing a Dean-Stark trap. To this solution was added 7.5 g (0.05 mole) of 2-mercaptohexanoic acid and the reaction mixture was heated at reflux for 5 hr. and then poured into a solution of 400 ml of water and 25 ml of concentrated ammonium hydroxide. The layers were separated and the organic layer was washed with 300 ml of water, twice with 300 ml portions of 2N hydrochloric acid, twice with 300 ml portions of water and dried (magnesium sulfate). The solvent was evaporated under reduced pressure and the light-yellow, viscous, oily residue was purified by high pressure liquid chromatography (Waters Associates Prep LC/System 500A; Prep-Pak ® 500 silica; ethyl acetate-hexanes, 1:6; flow rate 200 ml/min). Fractions containing the title isomer mixture were combined and the solvents evaporated under reduced pressure to yield 7.5 g (28%) of an orange, viscous oil as a (2:3) cis-trans isomeric mixture ($^{13}C$ NMR).

| Analysis calculated for: | $C_{31}H_{35}NO_5S$: C, 69.77; H, 6.61; N, 2.62 |
| --- | --- |
| | Found: C, 69.40; H, 6.61; N, 2.68 |

EXAMPLE 30

4-[3-[5-Butyl-4-oxo-2-(3-phenoxyphenyl)-3-thiazolidinyl]propoxy]benzoic acid cis-trans isomers.

To a stirred mixture of 7.1 g (0.013 mole) of 4-[3-[5-butyl-4-oxo-2-(3-phenoxyphenyl)-3-thiazolidinyl]propoxy]benzoic acid ethyl ester, cis-trans mixture in 500 ml of 95% ethanol was added a solution of 10.0 g (0.12 mole) of sodium bicarbonate in 100 ml of water and the reaction mixture was stirred and heated at reflux for 16 hr under a nitrogen atmosphere. The reaction mixture was filtered and the filtrate was evaporated under reduced pressure to give a solid residue. The solid was dissolved in 300 ml of water and the pH of the solution was adjusted to 2 with concentrated hydrochloric acid. The mixture was extracted with two 300 ml portions of ethyl ether. The ether extracts were washed with 300 ml of water, dried (magnesium sulfate) and the solvent was evaporated under reduced pressure to give 6.5 g (97%) of a viscous, oily residue. The residue was triturated with cold ethyl ether-petroleum ether (30°-60° C.). The resulting solid was collected by filtration to give 5.2 g (78%) of white solid, mp 90°-94° C., which is a (2:3) cis-trans isomeric mixture ($^{13}C$ NMR).

| Analysis calculated for: | $C_{29}H_{31}NO_5S$: C, 68.89; H, 6.18; N, 2.77 |
| --- | --- |
| | Found: C, 69.25; H, 6.58; N, 2.65 |

EXAMPLE 31

4-[3-[5-Butyl-4-oxo-2-(3-phenoxyphenyl)-3-thiazolidinyl]propoxy]benzoic acid ethyl ester trans isomer.

This compound was isolated (chromatography) in 15% yield (3.9 g) as a pure trans isomer (orange, viscous oil) in the preparation of the isomer mixture of Example 29. Rf (ethyl acetate-hexanes, 1:4; silica): 0.24.

| Analysis calculated for: | $C_{31}H_{35}NO_5S$: C, 69.77; H, 6.61; N, 2.62 |
| --- | --- |
| | Found: C, 69.49; H, 6.61; N, 2.64 |

EXAMPLE 32

4-[3-[5-Butyl-4-oxo-2-(3-phenoxyphenyl)-3-thiazolidinyl]propoxy]benzoic acid ethyl ester cis isomer.

This compound was isolated (chromatography) in 5% yield (1.3 g) as a pure cis isomer (golden, viscous oil) in the preparation of the isomer mixture of Example 29. R$_f$(ethyl acetate-hexanes, 1:4; silica): 0.28.

| Analysis calculated for: | $C_{31}H_{35}NO_5S$: C, 69.77; H, 6.61; N, 2.62 |
| --- | --- |
| | Found: C, 69.47; H, 6.63; N, 2.65 |

EXAMPLE 33

4-[3-[2-(3-Benzoylphenyl)-5-butyl-4-oxo-3-thiazolidinyl]propoxy]benzoic acid ethyl ester cis/trans (55:45) isomers.

A solution of 10.5 g (0.05 mole) of 3-benzoylbenzaldehyde, 11.2 g (0.05 mole) of 4-(3-aminopropoxy)benzoic acid ethyl ester and 7.5 g (0.05 mole) of 2-mercaptohexanoic acid in 300 ml of benzene was stirred and heated at reflux overnight utilizing a Dean-Stark trap.

The reaction mixture was poured into a solution of 400 ml of water and 20 ml of concentrated ammonium hydroxide. The layers were separated and the organic layer was washed with three 200-ml portions of water and dried (magnesium sulfate). The solvent was evaporated under reduced pressure to give 23.2 g (85%) of a brown, viscous oil. The oil was purified by high pressure liquid chromatography (Waters Associates Prep LC System/500A; PrepPak ® 500 silica; ethyl acetate-hexanes, 1:3).1 Fractions containing the product were combined and the solvents were evaporated under reduce pressure to give 10 g (37%) of slightly impure viscous, oil residue. An analytical sample was prepared by further purification of the above oily residue by high pressure liquid chromatography (using the above conditions) to give the title compound as a light-yellow, viscous oil which was determined to be a (55:45) cis-trans isomeric mixture ($^{13}$C NMR).

| Analysis calculated for: | $C_{32}H_{35}NO_5S$: | C, 70.43; H, 6.47; N, 2.57 |
| | Found: | C, 70.26; H, 6.49; N, 2.54 |

EXAMPLE 34

4-[3-[2-(3-Benzoylphenyl)-5-butyl-4-oxo-3-thiazolidinyl]propoxy]benzoic acid cis/trans (85:15) isomers.

To a solution of 4.7 g (0.0086 mole) of 4-[3-[5-butyl-4-oxo-2-(3-benzoylphenyl)-3-thiazolidinyl]propoxy]benzoic acid ethyl ester cis-trans isomeric mixture in 500 ml of 95% ethyl alcohol was added a solution of 10.0 g (0.119 mole) of sodium bicarbonate in 100 ml of water and the stirred reaction mixture was heated at reflux overnight under a nitrogen atmosphere. The solvents were evaporated under reduced pressure and the viscous residue was partitioned between water and ethyl ether (300 ml each). The aqueous layer was washed with two 300 ml portions of ethyl ether. The pH of the aqueous layer was adjusted to 2 with concentrated hydrochloric acid. The mixture was extracted with three 300 ml of water and dried (magnesium sulfate). The solvent was evaporated under reduced pressure and the viscous residue was treated with ethyl acetate-petroleum ether (30°-60° C.). The resulting solid (upon refrigeration) was collected by filtration to give 2.2 g (50%) of the title compound as a white solid, mp 140°-143° C., which was determined to be a (85:15) cis-trans isomeric mixture ($^{13}$C NMR).

| Analysis calculated for: | $C_{30}H_{31}NO_5S$: | C, 69.61; H, 6.04; N, 2.71 |
| | Found: | C, 69.30; H, 6.08; N, 2.69 |

EXAMPLE 35

5-Butyl-4-oxo-2-(3-phenoxypheny)-3-thiazolidineoctanoic acid ethyl ester cis/trans (3:2) isomers.

A solution of 6.4 g (0.032 mole) of 3-phenoxybenzaldehyde (Fluka), 6.0 g (0.032 mole) of 8-aminooctanoic acid ethyl ester[1] and 4.9 g (0.033 mole) of 2-mercaptohexanoic acid in 300 ml of benzene was stirred and heated at reflux overnight utilizing a Dean-Stark trap. The reaction mixture was poured into a solution of 400 ml of water and 20 ml of concentrated ammonium hydroxide. The layers were separated and the organic layer was washed successively with 200 ml of water, two 200 ml portions of 2N hydrochloride acid, and 200 ml of water, dried (magnesium sulfate), concentrated under reduced pressure, and the viscous, oily residue was purified by high pressure liquid chromatography (Waters Associates Prep LC/System 500A; PrepPak ® 500 silica; ethyl acetate-hexanes, 1:10; flow rate 200 ml/min). Fractions containing the product were combined and the solvents evaporated under reduced pressure to give 6.0 g (38%) of a yellow oil which was determined to be a (3:2) cis-trans isomeric mixture ($^{13}$C NMR).

| Analysis calculated for: | |
| --- | --- |
| $C_{29}H_{39}NO_4S$: | C, 69.99; H, 7.90; N, 2.81 |
| Found: | C, 69.69; H, 7.94; N, 2.86 |

[1]The amino ester was prepared in 41% yield as described in Preparation 20 from 1,3-dihydro-1,3-dioxo-2H-isoindole-2-octanoic acid ethyl ester.

EXAMPLE 36

4-[3-[5-Butyl-4-oxo-2-(3-phenoxypheny)-3-thiazolidinyl]propoxy]-3-methoxybenzeneacetic acid ethyl ester cis/trans (3:2) isomers.

A mixture of 6.5 g (0.033 mole) of 3-phenoxybenzaldehyde (Fluka) and 8.8 g (0.033 mole) of 4-(3-aminopropoxy)-3-methoxybenzene acetic acid ethyl ester in 250 ml of benzene was stirred and heated at reflux for 2 hr utilizing a Dean-Stark trap. To this mixture was added 4.9 g (0.03 mole) of 2-mercaptohexanoic acid and the mixture was heated at reflux overnight. The mixture was poured into a solution of 400 ml of water and 20 ml of concentrated ammonium hydroxide. The layers were separated and the organic layer was washed with two 300 ml of water, dried (magnesium sulfate), concentrated under reduced pressure, and the light-yellow, viscous residue was purified by high pressure liquid chromatography (Waters Associates Prep LC/System 500A; PrepPak ® 500 silica; ethyl acetate-hexanes, 1:3; flow rate 250 ml/min). Fractions containing the product were combined and the solvents were evaporated under reduced pressure to give 3.1 g (16%) of a yellow gum which is a (3:2) cis-trans isomeric mixture ($^{13}$C NMR).

| Analysis calculated for: | |
| --- | --- |
| $C_{33}H_{39}NO_6S$: | C, 68.61; H, 6.80; N, 2.42 |
| Found: | C, 68.19; H, 6.76; N, 2.37 |

EXAMPLE 37

4-[3-[5-Butyl-4-oxo-3-(3-phenoxypheny)-3-thiazolidinyl]propoxy]-3-methoxybenzoic acid methyl ester cis isomer.

A mixture of 4.9 g (0.025 mole) of 3-phenoxybenzaldehyde (Fluka), 5.9 g (0.025 mole) of 4-(3-aminopropoxy)-3-methoxybenzoic acid methyl ester (the amino ester was prepared by the procedure of Preparation 20 from 4-[3-(1,3-dihydro-1,3-dioxo-2H-isoindol-2-yl)propoxy-3-methoxybenzoic acid methyl ester) and 3.7 g (0.025 mole) of 2-mercaptohexanoic acid in 400 ml of benzene was stirred and heated at reflux overnight utilizing a Dean-Stark trap. The reaction mixture was poured into a solution of 400 ml of water and 20 ml of concentrated ammonium hydroxide. The layers were separated and the organic layer was washed successively with 300 ml of water, two 300 ml portions of 2N hydrochloric acid, 300 ml of water and dried (magnesium sulfate). The solvent was evaporated under reduced pressure and the residue was purified by high pressure liquid chromatography (Waters Associates Prep LC System/500A; PrepPak® 500 silica; ethyl acetate-hexanes, 1:3; flow rate 200 ml/min). Fractions containing the product were combined and the solvents were evaporated under reduced pressure to give 1.0 g (7%) of the title compound as a pure cis isomer ($^{13}C$ NMR). Concentration of other fractions gave 3.2 g of a (2:3) cis-trans isomeric mixture. The total yield of all isomers was 4.2 g (31%) with an isomeric ratio of (55:45) cis-trans population.

| Analysis calculated for: | |
|---|---|
| $C_{31}H_{35}NO_6S$: | C, 67.74; H, 6.42; N, 2.55 |
| Found: | C, 67.51; H, 6.37; N, 2.55 |

EXAMPLE 38

5-Butyl-4-oxo-2-(3-phenoxyphenyl)-3-thiazolidineoctanoic acid cis/trans (2:3) isomers.

To a stirred solution of 4.4 g (0.088 mole) of 5-butyl-4-oxo-2-(3-phenoxyphenyl)-3-thiazolidineoctanoic acid ethyl ester, cis-trans mixture (3:2) in 400 ml of ethanol was added a solution of 10.1 g (0.12 mole) of sodium bicarbonate in 100 ml of water and the reaction mixture was heated at reflux for 16 hr under a nitrogen atmosphere. The solvent was evaporated under reduced pressure and the residue was partitioned between water and ethyl ether (400 ml each). The aqueous layer was filtered and acidified to pH 2 with concentrated hydrochloric acid, and extracted with three 200 ml portions of methylene chloride. The organic extracts were washed with two 200 ml portions of water, dried (magnesium sulfate), and the solvent was evaporated under reduced pressure to give 4.0 g (98%) of a yellow gum which was determined to be a (2:3) cis-trans isomeric mixture ($^{13}C$ NMR).

| Analysis calculated for: | |
|---|---|
| $C_{27}H_{35}NO_4S$: | C, 69.05; H, 7.51; N, 2.98 |
| Found: | C, 69.03; H, 7.77; N, 3.01 |

EXAMPLE 39

4-[3-[5-Butyl-4-oxo-2-(3-phenoxyphenyl)-3-thiazolidinyl]propoxy]-3-methoxybenzoic acid cis/trans (2:3) isomers.

To a stirred solution of 3.0 g (0.055 mole) of 4-[3-[5-butyl-4-oxo-2-(3-phenoxyphenyl)-3-thiazolidinyl]propoxy]-3-methoxybenzoic acid methyl ester, cis-trans (2:3) in 300 ml of 95% ethanol was added a solution of 6.1 g (0.073 mole) of sodium bicarbonate in 100 ml of water and the mixture was heated at reflux overnight under a nitrogen atmosphere. The solvent was evaporated under reduced pressure and the residue was partitioned between water and ethyl ether (300 ml each). The layers were separated and the aqueous layer pH was adjusted to 2 with concentrated hydrochloric acid. The mixture was extracted with three 200 ml portions of methylene chloride and the combined organic extracts were washed with 300 ml of water, dried (magnesium sulfate), and the solvent was evaporated under reduced pressure to give 2.0 g (69%) of a yellow glass which was determined to be a (2:3) cis-trans isomeric mixture ($^{13}C$ NMR).

| Analysis calculated for: | |
|---|---|
| $C_{30}H_{33}NO_6S$: | C, 67.27; H, 6.21; N, 2.62 |
| Found: | C, 67.31; H, 6.27; N, 2.60 |

EXAMPLE 40

4-[3-[5-Butyl-4-oxo-2-(3-phenoxyphenyl)-3-thiazolidinyl]propoxy]-3-methoxybenzeneacetic acid cis/trans (2:3) isomers.

A solution of 4.4 g (0.052 mole) of sodium bicarbonate in 100 ml of water as added to a stirred solution of 2.3 g (0.004 mole) of 4-[3-[5-butyl-4-oxo-2-(3-phenoxyphenyl)-3-thiazolidinyl]propoxy]-3-methoxybenzeneacetic acid ethyl ester cis-trans (2:3) in 300 ml of 95% ethanol and the reaction mixture was heated at reflux overnight under a nitrogen atmosphere. The solvent was evaporated under reduced pressure and the residue was partitioned between water and ethyl ether (300 ml each). The layers were separated and the aqueous layer pH was adjusted to 2 with concentrated hydrochloric acid and the mixture was extracted with three 200 ml portions of methylene chloride. The methylene chloride extracts were washed with 300 ml of water, dried (magnesium sulfate) and the solvent evaporated under reduced pressure to give 1.7 g (77%) as a yellow gum which was determined to be a (2:3) cis-trans isomeric mixture ($^{13}C$ NMR).

| Analysis calculated for: | |
|---|---|
| $C_{31}H_{35}NO_6S$: | C, 67.74; H, 6.42; N, 2.55 |
| Found: | C, 65.79; H, 6.28; N, 2.37 |
| Calculated for $C_{31}H_{35}NO_6S \cdot 0.25CH_2Cl_2$: | C, 65.56; H, 6.30; N, 2.47 |

EXAMPLE 41

5-Butyl-4-oxo-2-(3-phenoxyphenyl)-3-thiazolidinepropanoic acid cis/trans (35:65) isomers.

A mixture of 5.9 g (0.03 mole) of 3-phenoxybenzaldehyde (Fluka), 2.8 g (0.03 mole) of β-alanine (98%, Aldrich) and 4.5 g (0.03 mole) of 2-mercaptohexanoic acid in 150 ml of benzene was stirred and heated at reflux overnight utilizing a Dean-Stark trap. The reaction mixture was washed with three 200 ml portions of water and the organic layer was dried (magnesium sulfate). The solvent was evaporated under reduced pressure to give 8.5 g of a viscous oil. The oil was partitioned between ethyl ether and a saturated sodium bicarbonate solution (300 ml each). The ether layer was further extracted with two 300 ml portions of saturated sodium bicarbonate solution. The combined aqueous layers pH was adjusted to 2 with concentrated hydrochloric acid and extracted with three 200 ml portions of ethyl ether. The combined ether extracts were washed with water (200 ml), dried (magnesium sulfate) and the solvent was evaporated under reduced pressure to give 5.6 g of a yellow, viscous oil. The above process (ethyl ether-sodium bicarbonate solution partitioning) was repeated, and then the solvent was evaporated under reduced pressure to give 2.9 g (24%) of a yellow gum which was determined to be a (35:65) cis-trans isomeric mixture ($^{13}C$ NMR).

| Analysis calculated for: | |
|---|---|
| $C_{22}H_{25}NO_4S$: | C, 66.14; H, 6.31; N, 3.51 |

-continued

| Found: | C, 64.60; H, 6.16; N, 3.44 |
| Analysis calculated for:<br>$C_{22}H_{25}NO_4S \cdot 0.15CH_2Cl_2$: | C, 64.54; H, 6.19; N, 3.40 |

EXAMPLE 42

5-Butyl-4-oxo-2-(3-phenoxyphenyl)-3-thiazolidineacetic acid cis/trans (2:3) isomers.

A mixture of 7.9 g (0.04 mole) of 3-phenoxybenzaldehyde (Fluka), 3.1 g (0.04 mole) of glycine (Fisher) and 6.1 g (0.04 mole) of 2-mercaptohexanoic acid in 150 ml of benzene was stirred and heated at reflux overnight utilizing a Dean-Stark trap. The reaction mixture was poured into 1 l of water. The layers were separated and the organic layer was washed twice with 300 ml of water, dried (magnesium sulfate), and the solvent was evaporated under reduced pressure to give 14.9 g of a yellow, viscous oil. The oil was purified by filtration through a silica gel column (10×30 cm glass column, 700 g of silica gel; methylene chloride). After washing the column with 3 l of methylene chloride, the silica gel was extracted with 3 l of methanol. The methanolic extracts were evaporated under reduced pressure and the viscous residue was partitioned between ethyl ether and a saturated sodium bicarbonate solution (500 ml each). The ether layer was further extracted with two 300 ml portions of a saturated sodium bicarbonate solution. The aqueous layer was washed with 300 ml of ethyl ether, and its pH was adjusted to 2 with concentrated hydrochloric acid. The mixture was extracted with three 300 ml portions of ethyl ether. The combined ether extracts were washed twice with 300 ml portions of water, dried (magnesium sulfate), and the solvent was evaporated under reduced pressure to give 11.6 g (75%) of the title compound as a yellow gum which is a (2:3) cis-trans isomeric mixture ($^{13}$C NMR).

| Analysis calculated for: | |
| --- | --- |
| $C_{21}H_{23}NO_4S$: | C, 65.43; H, 6.01; N, 3.63 |
| Found: | C, 64.93; H, 6.07; N, 3.64 |
| Analysis calculated for:<br>$C_{21}H_{23}NO_4S \cdot 0.25H_2O$: | C, 64.68; H, 6.07; N, 3.59 |

EXAMPLE 43

5-Butyl-4-oxo-2-(3-phenoxyphenyl)-3-thiazolidinehexanoic acid cis/trans (45:55) isomers.

A mixture of 8.7 g (0.044 mole) of 3-phenoxybenzaldehyde (Fluka), 5.8 g (0.044 mole) of ω-aminocaproic acid (Aldrich) and 6.5 g (0.044 mole) of 2-mercaptohexanoic acid in 200 ml of toluene was stirred and heated at reflux overnight utilizing a Dean-Stark trap. The reaction mixture was poured into 500 ml of water. The layers were separated and the organic layer was washed with 200 ml of 6N hydrochloric acid, twice with 200 ml portions of water and dried (magnesium sulfate). The solvent was evaporated under reduced pressure to give 16.2 g of a viscous oil. The oil was purified by filtration through a silica gel column (10×30 cm glass column; 600 g of silica; ethyl acetate-hexanes, 1:10). After washing the column with 3 l of this solvent mixture, the silica gel was extracted with 1.5 l of methanol. The methanolic extracts were evaporated under reduced pressure and the viscous residue was partitioned between methylene chloride and water (200 ml each). The organic layer was dried (magnesium sulfate), and the solvent evaporated under reduced pressure to give 9.2 g (47%) of a yellow gum which was determined to be a (45:55) cis-trans isomeric mixture ($^{13}$C NMR).

| Analysis calculated for: | |
| --- | --- |
| $C_{25}H_{31}NO_4S$: | C, 68.00; H, 7.08; N, 3.17 |
| Found: | C, 66.12; H, 6.96; N, 3.16 |
| Analysis calculated for:<br>$C_{25}H_{31}NO_4S \cdot 0.2CH_2Cl_2$: | C, 66.00; H, 6.90; N, 3.05 |

EXAMPLE 44

5-Butyl-4-oxo-2-(3-phenoxyphenyl)-3-thiazolidinepentanoic acid ethyl ester cis isomer.

A solution of 7.4 g (0.017 mole) of crude 5-butyl-4-oxo-2-(3-phenoxyphenyl)-3-thiazolidinepentanoic acid acid (prepared in 41% yield from 3-phenoxybenzaldehyde, 5-aminopentanoic acid, and 2-mercaptohexanoic acid according to procedure of Example 1), 2.7 g (0.017 mole) of 1,8-diazabicyclo[5.4.0]undec-7-ene (DBU, 96%, Aldrich) and 3.0 g (0.0192 mole) of iodoethane (99%, Aldrich) in 70 ml of benzene was stirred and heated at reflux for 30 min. The reaction mixture was filtered and the filtrate was washed successively with two 100 ml portions of water, two 100 ml portions of a saturated sodium bicarbonate solution, 100 ml of water, dried (magnesium sulfate) and the solvent was evaporated under reduced pressure to give 7.7 g of a viscous residue. The residue was purified by chromatography (3.5×90 cm glass column; 450 g of silica gel; ethyl acetate-hexanes, 1:10). Fractions containing the product were combined, and the solvents were evaporated under reduced pressure to give 3.1 g (38%) of ester as a viscous oil. The oil was further purified by high-pressure liquid chromatography (Waters Associates Prep LC/System 500A; PrepPak ® 500 silica; ethyl acetate-hexanes, 1:6; flow rate 150 ml/min). Fractions containing the title compound were combined and the solvents were evaporated under reduced pressure to give 0.3 g of the title compound as a yellow gum, Rf (Ethyl acetate:hexanes, 1:6; silica gel): 0.3[2.8 g of cis-trans (40:60)isomer mixture was also obtained].

| Analysis calculated for: | |
| --- | --- |
| $C_{26}H_{33}NO_4S$: | C, 68.54; H, 7.30; N, 3.07 |
| Found: | C, 68.10; H, 7.28; N, 3.10 |

EXAMPLE 45

5-Butyl-4-oxo-2-(3-phenoxyphenyl)-3-thiazolidinepentanoic acid cis/trans (40:60) isomer.

A solution of 6.1 g (0.07 mole) of sodium bicarbonate in 100 ml of water was added to a stirred solution of 2.8 g (0.006 mole) of 5-butyl-4-oxo-2-(3-phenoxyphenyl)-3-thiazolidinepentanoic acid ethyl ester, cis-trans (40:60) in 250 ml of 95% ethanol and the reaction mixture was heated at reflux under a nitrogen atmosphere for 16 hr. The solvent was evaporated under reduced pressure and the residue was partitioned between water and ethyl ether (200 ml each). The layers were separated and the aqueous layer was washed with 200 ml of ethyl ether. The aqueous layer pH was adjusted to 2 with concentrated hydrochloric acid and the mixture was extracted with two 200 ml portions of ethyl ether. The combined ether extracts were washed with 200 ml of water, dried (magnesium sulfate) and the solvent was evaporated under reduced pressure to give 1.9 g (73%) of the title compound as a yellow gum which is a (40:60) cis-trans isomeric mixture ($^{13}$C NMR).

| Analysis calculated for: | |
|---|---|
| $C_{24}H_{29}NO_4S$: | C, 67.42; H, 6.84; N, 3.28 |
| Found: | C, 64.91; H, 6.68; N, 3.21 |
| Calculated for: | C, 64.90; H, 6.63; N, 3.12 |
| $C_{24}H_{29}NO_4S.0.25CH_2Cl_2$: | |

EXAMPLE 46

5-Butyl-4-oxo-2-(3-phenoxyphenyl)-3-thiazolidineundecanoic acid cis/trans (45:55) isomer.

A mixture of 6.9 g (0.035 mole) of 3-phenoxybenzaldehyde (Fluka), 7.0 g (0.035 mole) of 11-aminoundecanoic acid (Aldrich) and 5.2 g (0.035 mole) of 2-mercaptohexanoic acid in 150 ml of toluene was stirred and heated at reflux overnight utilizing a Dean-Stark trap. The reaction mixture was poured into 400 ml of water. The layers were separated and the organic layer was dried (magnesium sulfate). The solvent was evaporated under reduced pressure and the yellow, viscous, oily residue was purified by chromatography (4.5×90 cm glass column; 500 g of silica gel; ethylacetate-hexanes, 1:4). Fractions containing the title compound were combined and the solvents were evaporated under reduced pressure to give 9.2 g (52%) of a yellow, viscous oil which is a (45:55) cis-trans isomeric mixture ($^{13}$C NMR).

| Analysis calculated for: | |
|---|---|
| $C_{30}H_{41}NO_4S$: | C, 70.42; H, 8.08; N, 2.74 |
| Found: | C, 70.11; H, 8.09; N, 2.73 |

EXAMPLE 47

4-[5-Butyl-4-oxo-2-(3-phenoxyphenyl)-3-thiazolidinylmethyl]benzoic acid ethyl ester cis/trans (55:45) isomers.

A solution of 6.4 g (0.014 mole) of 4-[5-butyl-4-oxo-2-(3-phenoxyphenyl)-3-thiazolidinylmethyl]benzoic acid (prepared in 38% yield from 3-phenoxybenzaldehyde (Fluka), 4-(aminomethyl)benzoic acid (97%, Aldrich) and 2-mercaptohexanoic acid by the procedure of Example 1), 2.2 g (0.014 mole) of 1,8-diazabicyclo[5.4.0]undec-7-ene (DBU, 96%, Aldrich) and 2.2 g (0.014 mole) of iodoethane (99%, Aldrich) in 120 ml of benzene was stirred and heated at reflux for 1 hr, poured into 200 ml of water and the layers were separated. The organic layer was further washed with two 200 ml portions of water, dried (magnesium sulfate), and the solvent was evaporated under reduced pressure to give 4.5 g of a viscous oil. The oil was purified by high-pressure liquid chromatography (Waters Associates Prep LC/System 500A; PrepPak ® 500 silica; ethyl acetate-hexanes, 1:7; flow rate 200 ml/min). Fractions containing the title compound were combined and the solvents evaporated under reduced pressure to give 3.3 g (49%) of the title compound as an off-white wax which is a (55:45) cis-trans isomeric mixture ($^{13}$C NMR).

| Analysis calculated for: | |
|---|---|
| $C_{29}H_{31}NO_4S$: | C, 71.14; H, 6.38; N, 2.86 |
| Found: | C, 69.87; H, 6.24; N, 2.85 |

-continued

| Analysis calculated for: | |
|---|---|
| $C_{29}H_{31}NO_4S.0.1CH_2Cl_2$: | C, 70.17; H, 6.31; N, 2.81 |

EXAMPLE 48

5-Butyl-4-oxo-2-(3-phenoxyphenyl)-3-thiazolidineundecanoic acid ethyl ester cis/trans (45:55) isomers.

A solution of 3.6 g (0.007 mole) of 5-butyl-4-oxo-2-(3-phenoxyphenyl)-3-thiazolidineundecanoic acid cis/trans (45:55), 1.2 g (0.0076 mole) of 1,8-diazabicyclo[5.4.0]undec-7-ene (DBU, 96%, Aldrich) and 1.2 g (0.0077 mole) of iodoethane (99%, Aldrich) in 100 ml of benzene was stirred and heated at reflux for 1 hr, filtered, and the filtrate washed with two 150 ml portions of water, dried (magnesium sulfate) and the solvent evaporated under reduced pressure to give 3.1 g of a viscous, oily residue. The oil was purified by high pressure liquid chromatography (Waters Associates Prep LC/Systems 500A; PrepPak ® 500 silica; ethyl acetate-hexanes, 1:7; flow rate 200 ml/min). Desired fractions were combined, and the solvents were evaporated under reduced pressure to give 1.5 g (39%) of the title compound as a yellow, viscous oil which is a (45:55) cis-trans isomeric mixture ($^{13}$C NMR).

| Analysis calculated for: | |
|---|---|
| $C_{32}H_{45}NO_4S$: | C, 71.21; H, 8.40; N, 2.60 |
| Found: | C, 71.02; H, 8.45; N, 2.62 |

EXAMPLE 49

5-Butyl-4-oxo-2-(3-phenoxyphenyl)-3-thiazolidinebutanoic acid ethyl ester cis isomer.

A solution of 25.7 g (0.062 mole) of 5-butyl-4-oxo-2-(3-phenoxyphenyl)-3-thiazolidine butyric acid (prepared in 78% yield from 3-phenoxybenzaldehyde (Fluka), 4-aminobutyric acid (Aldrich) and 2-mercaptohexanoic acid by the procedure of Example 1), 9.9 g (0.062 mole) of 1,8-diazabicyclo[5.4.0]undec-7-ene (DBU, 96%, Aldrich) and 9.8 g (0.062 mole) of iodoethane (99%, Aldrich) in 150 ml of benzene was stirred and heated at reflux for 1 hr, cooled, and the solid was removed by filtration. The filtrate was washed twice with 100 ml portions of water, dried (magnesium sulfate), and the solvent was evaporated under reduced pressure to give 25.3 g of a viscous, oily residue. The oil was purified by high pressure liquid chromatography (Waters Associates Prep LC/System 500A; PrepPak ® 500 silica; ethyl acetate-hexane, 1:7; flow rate 150 ml/min). Desired fractions were combined, and the solvents evaporated under reduced pressure to give 4.2 g (15%) of the title compound as a yellow, viscous oil that was determined to be the pure cis isomer by $^1$H and $^{13}$C NMR. Also obtained was 13.0 g (47%) of (1:3) cis-trans mixture and 1.3 g (5%) of pure trans isomer. Total yield: 18.5 g (68%) with a (46:54) cis-trans population ratio.

| Analysis calculated for: | |
|---|---|
| $C_{25}H_{31}NO_4S$: | C, 68.00; H, 7.08; N, 3.17 |
| Found: | C, 67.98; H, 7.09; N, 3.23 |

EXAMPLE 50

5-Butyl-4-oxo-2-(3-phenoxyphenyl)-3-thiazolidinehexanoic acid ethyl ester cis/trans (1:3) isomers.

This compound was isolated (chromatography) in 47% yield as a (1:3) cis-trans isomeric mixture (13C NMR; yellow, viscous oil) in the preparation of 5-butyl-4-oxo-2-(3-phenoxyphenyl)-3-thiazolidine butyric acid ethyl ester, cis isomer (Example 49).

| Analysis calculated for: | |
|---|---|
| $C_{25}H_{31}NO_4S$: | C, 68.00; H, 7.08; N, 3.17 |
| Found: | C, 67.81; H, 7.11; N, 3.23 |

EXAMPLE 51

5-Butyl-4-oxo-2-(3-phenoxyphenyl)-3-thiazolidinebutanoic acid ethyl ester cis isomer.

A mixture of 11.3 g (0.057 mole) of 3-phenoxybenzaldehyde (Fluka), 7.5 g (0.057 mole) of ω-aminocaproic acid (Aldrich) and 8.5 g (0.057 mole) of 2-mercaptohexanoic acid in 120 ml of toluene was stirred and heated at reflux for 6 hr utilizing a Dean-Stark trap. The reaction mixture was treated with 9.1 g (0.057 mole) of 1,8-diazabicyclo[5.4.0]undec-7-ene (DBU, 96%, Aldrich) and 9.0 g (0.0583 mole) of iodoethane (99%, Aldrich), and the mixture was stirred and heated at reflux for 1 hr, cooled, and the solid was removed by filtration. The filtrate was washed with two 200 ml portions of a saturated sodium bicarbonate solution and two 200 ml portions of water, dried (magnesium sulfate), and the solvent evaporated under reduced pressure to give 25.3 g (94%) of a viscous, oil residue. The oil was purified by high pressure liquid chromatography (Waters Associates Prep LC/System 500A; PrepPak® 500 silica; ethyl acetate-hexanes, 1:7; flow rate 150 ml/min). Fractions containing the desired product were combined, and the solvents were evaporated under reduced pressure to give 20.5 g (76%) of a viscous oil. The oily residue was further purified by chromatography (4×90 cm glass column; 470 g of silica gel; ethyl acetate-hexanes, 1:7). Fractions containing the title compound were combined, and the solvents were evaporated under reduced pressure to give 4.9 g (18%) of the title compound as a pure cis-isomer (13C and 1H NMR). $R_f$=0.31 on silica gel using ethyl acetate-hexane, 1:4. Also obtained was 13.4 g of a cis-trans isomer mixture (1:3 by 13C NMR) and 1.1 g of pure trans isomer for a total yield of 19.4 g (72%) with a 43:57 total cis-trans isomer population.

| Analysis calculated for: | |
|---|---|
| $C_{27}H_{35}NO_4S$: | C, 69.05; H, 7.51; N, 2.98 |
| Found: | C, 68.95; H, 7.49; N, 3.06 |

EXAMPLE 52

5-Butyl-4-oxo-2-(3-phenoxyphenyl)-3-thiazolidinehexanoic acid ethyl ester trans isomer.

This compound was isolated (chromatography) in 4% yield as a pure trans isomer (yellow, viscous oil) in the preparation of 5-butyl-4-oxo-2-(3-phenoxyphenyl)-3-thiazolidinehexanoic acid ethyl ester, cis isomer. Rf=0.26 on silica gel using ethyl acetate-hexane, 1:4.

| Analysis calculated for: | |
|---|---|
| $C_{27}H_{35}NO_4S$: | C, 69.05; H, 7.51; N, 2.98 |
| Found: | C, 68.92; H, 7.49; N, 3.03 |

EXAMPLE 53

5-Butyl-4-oxo-2-(3-phenoxyphenyl)-3-thiazolidinehexanoic acid ethyl ester cis/trans (1:3) isomers.

This compound was isolated (chromatography) in 50% yield as a (1:3) cis-trans isomeric mixture (13C NMR; yellow, viscous oil) in the preparation of 5-butyl-4-oxo-2-(3-phenoxyphenyl)-3-thiazolidinehexanoic acid ethyl ester, cis isomer.

| Analysis calculated for: | |
|---|---|
| $C_{27}H_{35}NO_4S$: | C, 69.05; H, 7.51; N, 2.98 |
| Found: | C, 68.86; H, 7.55; N, 3.05 |

EXAMPLE 54

5-Butyl-4-oxo-2-(3-phenoxyphenyl)-3-thiazolidinebutanoic acid cis/trans (1:2) isomers.

To a stirred solution of 8.6 g (0.02 mole) of 5-butyl-4-oxo-2-(3-phenoxyphenyl)-3-thiazolidinebutanoic acid ethyl ester, cis-trans isomer in 450 ml of 95% ethanol was added a solution of 20.2 g (0.24 mole) of sodium bicarbonate in 140 ml of water, and the mixture was heated at reflux for 16 hr under a nitrogen atmosphere. The solvents were evaporated under reduced pressure, and the residue was partitioned between ethyl ether and water (250 ml each). The aqueous layer was washed further with two 200 ml portions of ethyl ether, acidified to pH 2 with concentrated hydrochloric acid, and then the mixture was extracted with three 200 ml portions of water, dried (magnesium sulfate), and the solvent evaporated under reduced pressure to give 6.4 g (80%) of the title compound as a yellow, viscous oil which is a (1:2) cis-trans isomeric mixture (13C NMR).

| Analysis calculated for: | |
|---|---|
| $C_{23}H_{27}NO_4S$: | C, 66.80; H, 6.58; N, 3.39 |
| Found: | C, 66.19; H, 6.53; N, 3.35 |
| Analysis calculated for: | C, 66.08; H, 6.63; N, 3.35 |
| $C_{23}H_{27}NO_4S.0.25H_2O$: | |

EXAMPLE 55

5-Butyl-4-oxo-2-(3-phenoxyphenyl)-3-thiazolidineheptanoic acid ethyl ester cis/trans isomers.

A solution of 10.9 g (0.024 mole) of 5-butyl-4-oxo-2-(3-phenoxyphenyl)-3-thiazolidineheptanoic acid (prepared in 92% yield from 3-phenoxybenzaldehyde (Fluka), 7-aminoheptanoic acid (Aldrich) and 2-mercaptohexanoic acid by the procedure of Example 1), 4.0 g (0.025 mole) of 1,8-diazabicyclo[5.4.0]undec-7-ene (DBU, 96%, Aldrich) and 4.1 g (0.026 mole) of iodoethane (99%, Aldrich) in 100 ml of toluene was stirred and heated at reflux for 2 hr, cooled, and the solid was removed by filtration. The filtrate was washed with 300 ml of water, two 300 ml portions of a saturated sodium bicarbonate solution, dried (magnesium sulfate), and the solvent evaporated under reduced pressure to give 8.3 g (72%) of a yellow, viscous oil. The oil was purified by chromatography (4×90 cm glass column; 470 g of silica gel; ethyl acetate-hexane, 1:4). Desired fractions were combined, and the solvents were evaporated under reduced pressure to give 7.1 g (61%) of the title compound as a light-yellow, viscous oil is a (1:1) cis-trans isomeric mixture ($^{13}$C NMR).

| Analysis calculated for: | |
|---|---|
| $C_{28}H_{37}NO_4S$: | C, 69.53; H, 7.71; N, 2.90 |
| Found: | C, 69.56; H, 7.73; N, 2.96 |

EXAMPLE 56

5-Butyl-4-oxo-2-(3-phenoxyphenyl)-3-thiazolidineheptanoic acid cis/trans (2:3) isomers.

To a solution of 4.9 g (0.01 mole) of 5-butyl-4-oxo-2-(3-phenoxyphenyl)-3-thiazolidineheptanoic acid ethyl ester in 350 ml of 95% ethanol was added a solution of 10.1 g (0.12 mole) of sodium bicarbonate in 120 ml of water and the mixture was stirred and heated at reflux overnight under a nitrogen atmosphere. The solvents were evaporated under reduced pressure and the residue was partitioned between ethyl ether and water (250 ml each). The aqueous layer was further extracted with 250 ml of ether (the ether extracts were discarded). The aqueous layer pH was adjusted to 2 with concentrated hydrochloric acid and the mixture was extracted with three 250 ml portions of ethyl ether. The combined ether extracts were washed with two 300 ml portions of water, dried (sodium sulfate) and the solvent was evaporated under reduced pressure to give 3.4 g (74%) of the title compound as a yellow gum which is a (2:3) cis-trans isomeric mixture ($^{13}$C NMR).

| Analysis calculated for: | |
|---|---|
| $C_{26}H_{33}NO_4S$: | C, 68.54; H, 7.30; N, 3.07 |
| Found: | C, 68.14; H, 7.32; N, 3.10 |

EXAMPLE 57

4-[5-Butyl-4-oxo-2-(3-phenoxyphenyl)-3-thiazolidinylmethyl]benzoic acid cis/trans (1:1) isomers.

To a solution of 4.2 g (0.086 mole) of 4-[5-butyl-4-oxo-2-(3-phenoxyphenyl)-3-thiazolidinylmethyl]benzoic acid ethyl ester in 250 ml of 95% ethanol was added a solution of 8.6 g (0.07 mole) of sodium bicarbonate in 100 ml of water and the mixture was stirred and heated at reflux for 6 hr, filtered, and the filtrate was evaporated under reduced pressure to give a viscous residue. The residue was partitioned between ethyl ether and water (300 ml each). The aqueous layer was further extracted with 300 ml of ethyl ether and the ether extracts were discarded. The aqueous layer pH was adjusted to 2 with concentrated hydrochloric acid and the mixture was extracted with three 200 ml portions of ethyl ether. The combined ether extracts were washed with 300 ml of water, dried (magnesium sulfate) and the solvent was evaporated under reduced pressure to give 2.9 g of a viscous residue. The residue was triturated with ethyl ether-petroleum ether (30°-60° C.) and the resulting solid was collected by filtration. The solid was recrystallized from ethyl ether-petroleum ether (30°-60° C.) to give 2.0 g (51%) of the title compound as a white solid, mp 122°-124° C. which is a (1:1) cis-trans isomeric mixture ($^{13}$C NMR).

| Analysis calculated for: | |
|---|---|
| $C_{27}H_{27}NO_4S$: | C, 70.26; H, 5.90; N, 3.03 |
| Found: | C, 70.12; H, 5.83; N, 3.14 |

EXAMPLE 58

5-Butyl-2-(1,1'-biphenyl-4-yl)-3-(4-phenylbutyl)-4-thiazolidinone cis/trans (1:3) isomers.

A solution of 13.0 g (0.066 mole) of 4-biphenylcarboxyaldehyde (99%, Aldrich), 10.4 g (0.0697 mole) of 4-phenylbutylamine (Aldrich) and 10.5 g (0.071 mole) of 2-mercaptohexanoic acid in 250 ml of benzene was stirred and heated at reflux overnight utilizing a Dean-Stark trap. The reaction mixture was poured into a solution of 400 ml of water and 18 ml of concentrated ammonium hydroxide. The layers were separated and the organic layer was washed with two 300 ml portions of 2N hydrochloric acid, two 300 ml portions of water and dried (magnesium sulfate). The solvent was evaporated under reduced pressure and the viscous, oily residue was purified by high pressure liquid chromatography (Waters Associates Prep LC/System 500A; Prep-Pak ® 500 Silica; ethyl acetate-hexanes, 1:20; flow rate: 150 ml/min). Desired fractions were combined and the solvents evaporated under reduced pressure to give 24.6 g of viscous, oily residue. The residue was purified further by chromatography (4.5×90 cm glass column; 500 g of silica; ethyl acetate-hexanes, 1:8). Fractions containing the product were combined and the solvents evaporated under reduced pressure to yield 20.9 g (67%) of the title compound as a yellow, viscous oil which is a (1:3) cis-trans isomeric mixture ($^{13}$C NMR).

| Analysis calculated for: | |
|---|---|
| $C_{29}H_{33}NOS$: | C, 78.51; H, 7.50; N, 3.16 |
| Found: | C, 78.31; H, 7.54; N, 3.16 |

EXAMPLE 59

5-Butyl-3-[2-(4-hydroxyphenyl)ethyl]-2-(3-phenoxyphenyl)-4-thiazolidinone cis/trans (2:3).

A mixture of 13.9 g (0.07 mole) of 3-phenoxybenzaldehyde (Fluka), 9.9 g (0.070 mole) of tyramine (97%, Aldrich), and 10.5 g (0.07 mole) of 2-mercaptohexanoic acid (81504-86-1) in 250 ml of benzene was stirred and heated at reflux overnight utilizing a Dean-Stark trap. The reaction mixture was poured into a solution of 400 ml of water and 18 ml of concentrated ammonium hydroxide. The layers were separated and the organic layer was washed with two 300 ml portions of water, dried (magnesium sulfate) and the solvent evaporated under reduced pressure to give a viscous oil that solidified upon standing. The solid was purified by chromatography (4.5×90 cm glass column; 500 g of silica; methylene chloride). The desired fractions were combined and the solvent was evaporated under reduced pressure. The residue was recrystallized twice from benzene-cyclohexane to yield 10.5 g (34%) of the title compound as a white solid, mp 128°-131° C., which is a (2:3) cis-trans isomeric mixture ($^{13}$C NMR).

| Analysis calculated for: | |
|---|---|
| $C_{27}H_{29}NO_3S$: | C, 72.45; H, 6.53; N, 3.13 |

| Found: | C, 72.66; H, 6.58; N, 3.15 |

EXAMPLE 60

5-Butyl-2-(3-phenoxyphenyl)-3-(5-phenylpentyl)-4-thiazolidinone cis/trans (2:3) isomers.

This compound was prepared by the procedure of Example 58. Thus a solution of 9.1 g (0.046 mole) of 3-phenoxybenzaldehyde (Fluka), 7.5 g (0.0459 mole) of 5-phenylpentylamine and 6.8 g (0.046 mole) of 2-mercaptohexanoic acid in 250 ml of benzene gave 18.3 g of a yellow, viscous oil. The oil was purified by chromatography (4.5×90 cm glass column, 500 g of silica, ethyl acetate-hexanes, 1:13). Fractions containing the desired compound were combined and the solvents evaporated under reduced pressure to yield 11.9 g (55%) of the title compound as a yellow, viscous oil which is a (2:3) cis-trans isomeric mixture ($^{13}$C NMR).

| Analysis calculated for: | |
|---|---|
| $C_{30}H_{35}NO_2S$: | C, 76.07; H, 7.45; N, 2.96 |
| Found: | C, 75.76; H, 7.47; N, 3.00 |

EXAMPLE 61

5-Butyl-2-(2-naphthalenyl)-3-(4-phenylbutyl)-4-thiazolidinone cis/trans (35:65) isomers.

This compound was prepared by the procedure of Example 58. Thus, a solution of 12.8 g (0.08 mole) of 2-naphthaldehyde (98%, Aldrich), 12.2 g (0.08 mole) of 4-phenylbutylamine (98%, Aldrich), and 12.0 g (0.08 mole) of 2-mercaptohexanoic acid in 250 ml of benzene gave a yellow, viscous residue. The residue was purified by chromatography (4.5×90 cm glass column; 500 g of silica; ethyl acetate-hexanes, 1:13). Fractions containing the product were combined and the solvents evaporated under reduced pressure to yield 17.4 g (52%) of the title compound as a pale-orange, viscous oil which is a (35:65) cis-trans isomeric mixture ($^{13}$C NMR).

| Analysis calculated for: | |
|---|---|
| $C_{27}H_{31}NOS$: | C, 77.66; H, 7.48; N, 3.35 |
| Found: | C, 77.89; H, 7.68; N, 3.38 |

EXAMPLE 62

5-Butyl-3-(4-phenylbutyl)-2-[4-(phenylmethoxy)phenyl]-4-thiazolidinone cis/trans (45:55) isomers.

This compound was prepared by the procedure used in Example 58. Thus, a solution of 14.9 g (0.07 mole) of 4-benzyloxybenzaldehyde (Aldrich), 10.7 g (0.07 mole) of 4-phenylbutylamine (98%, Aldrich), and 10.5 g (0.07 mole) of 2-mercaptohexanoic acid in 250 ml of benzene gave a yellow, viscous oil. The oil was purified by chromatography (4.5×105 cm glass column; 500 g of silica; methylene chloride). Fractions containing the product were combined and the solvent evaporated under reduced pressure to yield 22.2 g (67%) of the title compound as a pale-orange, viscous oil which is a (45:55) cis-trans isomeric mixture ($^{13}$C NMR).

| Analysis calculated for: | |
|---|---|
| $C_{30}H_{35}NO_2S$: | C, 76.07; H, 7.45; N, 2.96 |
| Found: | C, 74.96; H, 7.44; N, 2.69 |
| Analysis calculated for: | C, 74.98; H, 7.36; N, 2.91 |
| $C_{30}H_{35}NO_2S \cdot 0.1CH_2Cl_2$: | |

EXAMPLE 63

5-Butyl-2-(4-phenoxyphenyl)-3-[4-(phenylbutyl]-4-thiazolidinone cis/trans (1:2) isomers.

This compound was prepared by the procedure used in Example 58. Thus, a solution of 10.3 g (0.05 mole) of 4-phenoxybenzaldehyde (98%, Aldrich), 7.8 g (0.05 mole) of 4-phenylbutylamine (98%, Aldrich), and 7.6 g (0.05 mole) of 2-mercaptohexanoic acid in 250 ml of benzene gave a yellow, viscous residue. The residue was purified by chromatography (4.5×105 cm glass column; 500 g of silica; ethyl acetate-hexanes, 1:10). Desired fractions were combined and the solvents evaporated under reduced pressure to yield 10.6 g (45%) of the title compound as a yellow, viscous oil which is a (1:2) cis-trans isomeric mixture ($^{13}$C NMR). Also obtained was 3.0 g (13%) of the pure cis-isomer and 2.6 g (11%) of the pure trans-isomer. Total yield: 16.2 g (69%) with a (40:60) cis-trans population ratio.

| Analysis calculated for: | |
|---|---|
| $C_{29}H_{33}NO_2S$: | C, 75.78; H, 7.23; N, 3.05 |
| Found: | C, 76.19; H, 7.34; N, 3.13 |

EXAMPLE 64

5-Butyl-3-[(4-hydroxyphenyl)methyl]-2-(3-phenoxyphenyl)-4-thiazolidinone cis/trans (55:45) isomers.

To a solution of 10.0 g (0.02 mole) of 5-butyl-3-(4-methoxyphenylmethyl)-2-(3-phenoxyphenyl)-4-thiazolidinone in 120 ml of methylene chloride was added a solution of 28.0 g (0.09 mole) of borontribromidemethylsulfide complex (Aldrich) in 200 ml of methylene chloride and the reaction mixture was stirred and heated at reflux for 12 hr then stirred at ambient temperature for 6 hr. The reaction mixture was treated with 200 ml of water and the layers were separated. The organic layer was washed successively with two 200 ml portions of water, two 300 ml portions of saturated sodium bicarbonate solution, 300 ml of water, dried (magnesium sulfate) and the solvent was evaporated under reduced pressure to give 11.1 g of a dark, viscous residue. This residue was purified by high-pressure, liquid chromatography (Waters Associates Prep LC/System 500A; PrepPak ® 500/silica; ethyl acetate-hexanes, 1:4, flow rate 200 ml/min). Desired fractions were combined and the solvents evaporated under reduced pressure to give 9.4 g (97%) of a viscous oil. The oil was dissolved in acetone, treated with charcoal, and filtered through Celite ®. The filtrate was evaporated under reduced pressure to yield 9.2 g (95%) of the title compound as a yellow, viscous oil (brown glass after drying) which is a (55:45) cis-trans isomeric mixture ($^{13}$C NMR).

| Analysis calculated for: | $C_{26}H_{27}NO_3S$: C, 72.03; H, 6.28; N, 3.23 |
|---|---|
| | Found: C, 70.89; H, 6.33; N, 3.17 |
| Calculated for: | |
| $C_{26}H_{27}NO_3S \cdot 0.6C_3H_6O$ (acetone): | C, 71.28; H, 6.58; N, 2.99 |

EXAMPLE 65

[4-[5-Butyl-4-oxo-2-(3-phenoxyphenyl)-3-thiazolidinylmethyl)phenoxy]acetic acid ethyl ester cis/trans (1:1) isomers.

A mixture of 21.2 g (0.049 mole) of crude 5-butyl-3-[(4-hydroxyphenyl)methyl]-2-(3-phenoxyphenyl)-4-thiazalidinone (Example 64), 12.5 g (0.073 mole) of ethyl bromoacetate (97%, Aldrich), and 13.5 g (0.098 mole) of potassium carbonate in 300 ml of acetone was vigorously stirred and heated at reflux overnight. The reaction mixture was filtered, and the filtrate was evaporated under reduced pressure to give 28.5 g of a viscous residue. The residue was purified by chromatography (4.5 × 105 cm glass column; 500 g of silica gel; ethyl acetate-hexanes, 1:4). Fractions containing the product were combined and the solvents were evaporated under reduced pressure to give 24.6 g (97%) of the title compound as a pale-yellow gum which is a (1:1) cis-trans isomeric mixture ($^{13}$C NMR).

| Analysis calculated for: | $C_{30}H_{33}NO_5S$: C, 69.34; H, 6.40; N, 2.70 |
| --- | --- |
| | Found: C, 68.66; H, 6.42; N, 2.71 |
| Analysis calculated for: | |
| $C_{30}H_{33}NO_5S \cdot 0.1CH_2Cl_2$: | C, 68.45; H, 6.34; N, 2.65 |

EXAMPLE 66

5-Butyl-2-(3-phenoxyphenyl)-3-(4-phenylbutyl)-4-thiazolidinone S,S-dioxide cis/trans (1:3) isomers.

To a stirred, cooled (ice water, 0° C.) solution of 9.1 g (0.02 mole) of 5-butyl-2-(3-phenoxyphenyl)-3-(4-phenylbutyl)-4-thiazolidinone cis-trans (2:3) mixture (Example 1) in 150 ml of methylene chloride was added, dropwise over a 30 min period, a solution of 7.8 g (0.045 mole) of m-chloroperbenzoic acid in 150 ml of methylene chloride. The reaction mixture was stirred at ambient temperature for 4 hr, diluted with 300 ml of methylene chloride and then washed with three 200 ml portions of a 10% sodium bicarbonate solution, twice with 200 ml portions of water and dried (magnesium sulfate). The solvent was evaporated under reduced pressure and the light yellow, viscous, oily residue was purified by chromatography (4.5 × 110 cm glass column; 500 g of silica gel; ethyl acetate-hexanes, 1:10). Fractions containing the product were combined and the solvents evaporated under reduced pressure to give 6.2 g (64%) of the title compound as a light-yellow, viscous oil which is (1:3) mixture of cis-trans isomers ($^{13}$C NMR).

| Analysis calculated for: | $C_{29}H_{33}NO_4S$: C, 70.85; H, 6.77; N, 2.85 |
| --- | --- |
| | Found: C, 70.77; H, 6.81; N, 2.85 |

EXAMPLE 67

4-[3-[2-(3-Benzoylphenyl)-5-butyl-4-oxo-3-thiazolidinyl]propoxy]benzoic acid ethyl ester S,S-dioxide cis/trans (65:35) isomers.

To a stirred, cooled (ice water, 0° C.) solution of 4.5 g (0.008 mole) of 4-[3-[2-(3-benzoylphenyl)-5-butyl-4-oxo-3-thiazolidinyl]propoxy]benzoic acid ethyl ester cis-trans isomer in 70 ml of methylene chloride was added, dropwise over a 10 min period, a solution of 3.3 g (0.02 mole) m-chloroperbenzoic acid in 70 ml of methylene chloride and the reaction mixture was stirred at ambient temperature for 3 hr. To the reaction mixture was added 200 ml of methylene chloride and the mixture was washed twice with 300 ml portions of a saturated sodium bicarbonate solution, twice with 300 ml portions of water and dried (magnesium sulfate). The solvent was evaporated under reduced pressure to give 4.7 g (98%) of a yellow, viscous oil that solidified upon standing. The solid was purified by chromatography (4.5 × 90 cm glass column; 490 g of silica, ethyl acetate-hexanes, 1:3). Fractions containing the product were combined and the solvents were evaporated under reduced pressure to give 4.1 g (85%) of the title compound as a semi-solid which is a (65:35) cis-trans isomeric mixture ($^{13}$C NMR).

| Analysis calculated for: | $C_{32}H_{35}NO_7S$: C, 66.53; H, 6.11; N, 2.43 |
| --- | --- |
| | Found: C, 66.38; H, 6.18; N, 2.35 |

EXAMPLE 68

5-Butyl-4-oxo-2-(3-phenoxyphenyl)-3-thiazolidinehexanoic acid ethyl ester S,S-dioxide cis/trans (1:1) isomers.

To a stirred solution of 13.0 g (0.028 mole) of 5-butyl-4-oxo-2-(3-phenoxyphenyl)-3-thiazolidinehexanoic acid ethyl ester, cis-trans mixture in 150 ml of methylene chloride was added, dropwise over a 20 min period, a solution of 13.0 g (0.063 mole) of m-chloroperbenzoic acid (80-85%, Aldrich) in 100 ml of methylene chloride. The reaction mixture was stirred at ambient temperature for 2 hr, washed with three 30 ml portions of a saturated sodium bicarbonate solution, twice with 300 ml portions of water, dried (magnesium sulfate), and the solvent was evaporated under reduced pressure to give 11.7 g (84%) of a light-yellow, viscous oil. The oil was purified by chromatography (4 × 90 cm glass column; 500 g of silica gel; ethyl acetate-hexane, 1:4). Fractions containing the product were combined, and the solvents were evaporated under reduced pressure to give 9.7 g (70%) of the title compound as a light-yellow, viscous oil which is a (1:1) cis-trans isomeric mixture ($^{13}$C NMR).

| Analysis calculated for: | $C_{27}H_{35}NO_6S$: C, 64.65; H, 7.03; N, 2.79 |
| --- | --- |
| | Found: C, 64.35; H, 7.00; N, 2.85 |

EXAMPLE 69

5-Butyl-4-oxo-2-(3-phenoxyphenyl)-3-thiazolidinebutanoic acid ethyl ester S,S-dioxide cis/trans (3:2) isomers.

To a stirred solution of 4.4 g (0.01 mole) of 5-butyl-4-oxo-2-(3-phenoxyphenyl)-3-thiazolidinebutanoic acid ethyl ester cis-trans isomer in 75 ml of methylene chloride was added dropwise, over a 10 min period, a solution of 7.4 g (0.023 mole) of m-chloroperbenzoic acid (80-85%, Aldrich) in 70 ml of methylene chloride. The reaction mixture was stirred at ambient temperature for 3 hr, diluted with 200 ml of methylene chloride, and then washed with four 200 ml portions of a saturated sodium bicarbonate solution, twice with 200 ml portions of water, and dried (magnesium sulfate). The solvent was evaporated under reduced pressure, and the viscous residue was purified by chromatography (4 × 90 cm glass column; 420 g of silica gel; ethyl acetate-hexanes, 1:4). Fraction containing the product were combined, and the solvents were evaporated under reduced pressure to give 2.5 g (53%) of the title compound as a light-yellow gum which is a (3:2) cis-trans isomeric mixture ($^{13}$C NMR).

| Analysis calculated for: | $C_{25}H_{31}NO_6S$: C, 63.40; H, 6.60; N, 2.96 |
|---|---|
| | Found: C, 63.28; H, 6.62; N, 2.98 |

EXAMPLE 70

5-Butyl-4-oxo-2-(3-phenoxyphenyl)-3-thiazolidinehexanoic acid S,S-dioxide cis/trans (3:2) isomers.

To a stirred solution of 6.0 g (0.012 mole) of 5-butyl-4-oxo-2-(3-phenoxyphenyl)-3-thiazolidinehexanoic acid ethyl ester S,S-dioxide in 350 ml of 95% ethanol was added a solution of 12.2 g (0.145 mole) of sodium bicarbonate in 120 ml of water, and the mixture was heated at reflux for 20 hr under a nitrogen atmosphere. The solvent was evaporated under reduced pressure, and the residue was partitioned between ethyl ether and water (300 ml each). The layers were separated, and the aqueous layer was further extracted with two 300 ml portions of ethyl ether. The aqueous layer pH was adjusted to 2 with concentrated hydrochloric acid, and the mixture was extracted with three 300 ml portions of ethyl ether. The combined ether extracts were washed with 300 ml of water, dried (magnesium sulfate), and the solvent was evaporated under reduced pressure to give 2.9 g (51%) of the title compound as a yellow, viscous oil which is a (3:2) cis-trans isomeric mixture ($^{13}$C NMR).

| Analysis calculated for: | $C_{25}H_{31}NO_6S$: C, 63.40; H, 6.60; N, 2.96 |
|---|---|
| | Found: C, 61.38; H, 6.56; N, 3.02 |
| Analysis calculated for $C_{25}H_{31}NO_6S.0.2CH_2Cl_2$: | |
| | C, 61.70; H, 6.45; N, 2.86 |

EXAMPLE 71

5-Butyl-2-(3-phenoxyphenyl)-4-oxo-3-thiazolidinehexanoic acid S-oxide.

A solution of 5-butyl-4-oxo-3-(3-phenoxyphenyl)-3-thiazolidinehexanoic acid ethyl ester cis-trans (1:3) (4.95 g, 0.010 mole) and sodium perborate tetrahydrate (1.54 g, 0.010 mole) in glacial acetic acid (100 ml) is stirred at room temperature for 18 hr. The mixture is concentrated in vacuo and the residual material partitioned between methylene chloride and 2N sodium hydroxide solution. The methylene chloride solution is concentrated in vacuo and the residue dissolved in ethanol (150 ml). This solution is added to 100 ml of 10% aqueous sodium bicarbonate solution and the mixture heated at reflux temperature under a nitrogen atmosphere for 20 hr. The mixture is concentrated in vacuo and the residue partitioned between methylene chloride and water (200 ml each). The aqueous layer is acidified to pH 2 by addition of concentrated hydrochloric acid and extracted with three 200 ml portions of methylene chloride. The combined extract is dried (magnesium sulfate) and concentrated to obtain the title compound.

EXAMPLE 72

5-Butyl-2-(3-phenoxyphenyl)-3-(2-pyridinylmethyl)-4-thiazolidinone cis isomer.

This compound was isolated (chromatography) in 15% yield as the cis isomer (yellow, viscous oil) in the preparation of 5-butyl-2-(3-phenoxyphenyl)-3-(2-pyridinylmethyl)-4-thiazolidinone cis-trans (1:4). Rf (ethyl acetate-hexanes, 1:3, silica): 0.29.

| Analysis calculated for: | $C_{25}H_{26}N_2O_2S$: C, 71.74; H, 6.26; N, 6.69 |
|---|---|
| | Found: C, 71.68; H, 6.23; N, 6.63 |

EXAMPLE 73

5-Butyl-2-(3-phenoxyphenyl)-3-(2-pyridinylmethyl)-4-thiazolidinone cis/trans (1:4) isomers.

A stirred solution of 11.9 g (0.06 mole) of 3-phenoxybenzaldehyde (Fluka), 6.6 g (0.06 mole) of 2-(aminomethyl)pyridine (99%, Aldrich) in 150 ml of benzene was heated at reflux temperature for 2 hr utilizing a Dean-Stark trap. To this mixture was added 8.9 g (0.06 mole) of 2-mercaptohexanoic acid and the mixture heated at reflux temperature for 6 hr. The reaction mixture was poured into a solution of 20 ml of concentrated ammonium hydroxide and 400 ml of water. The benzene layer was washed with three 300 ml portions of water and dried over magnesium sulfate. The solution was concentrated under reduced pressure to obtain a yellow-orange viscous oil. The oil was purified by chromatography (4.5 × 105 cm glass column; 500 g of silica; ethyl acetate-hexanes 1:3) to yield 3.8 g (15%) of the pure cis isomer (Example 72), 4.4 g (18%) of the pure trans isomer (Example 74) and 6.4 g (25%) of the title compound (cis/trans 1:4 by $^{13}$C NMR). The total yield was 14.6 g (58%) with a 34:66 cis-trans population ratio.

| Analysis calculated for: | $C_{25}H_{26}N_2O_2S$: C, 71.74; H, 6.26; N, 6.69 |
|---|---|
| | Found: C, 71.48; H, 6.23; N, 6.64 |

EXAMPLE 74

5-Butyl-2-(3-phenoxyphenyl)-3-(2-pyridinylmethyl)-4-thiazolidinone trans isomer.

This compound (trans isomer) was isolated (chromatography) in 18% yield as a yellow, viscous oil in the preparation of Example 73. Rf (ethyl acetate-hexanes, 1:3; silica): 0.20.

| Analysis calculated for: | $C_{25}H_{26}N_2O_2S$: C, 71.74; H, 6.26; N, 6.69 |
|---|---|
| | Found: C, 71.77; H, 6.24; N, 6.65 |

EXAMPLE 75

2-(3-Phenoxyphenyl)-5-phenyl-3-[2-(2-pyridinyl)ethyl]-4-thiazolidinone cis isomer.

The title compound (cis-isomer) was isolated by chromatography in 17% yield as a light-orange gum in the preparation of 2-(3-phenoxyphenyl)-5-phenyl-3-[2-(2-pyridinyl)ethyl]-4-thiazolidinone, cis-trans (1:9). Rf (ethyl acetate-hexanes, 1:1; silica): 0.27.

| Analysis calculated for: | $C_{28}H_{24}N_2O_2S$: C, 74.31; H, 5.35; N, 6.19 |
|---|---|
| | Found: C, 74.13; H, 5.30; N, 6.21 |

EXAMPLE 76

2-(3-Phenoxyphenyl)-5-phenyl-3-[2-(2-pyridinyl)ethyl]-4-thiazolidinone cis/trans (1:9) isomers.

This compound was prepared by the procedure used in Example 73. Thus, a solution of 17.6 g (0.089 mole) of 3-phenoxybenzaldehyde (Fluka), 14.9 g (0.089 mole) of α-mercaptophenylacetic acid and 10.8 g (0.088 mole) of 2-(2-aminoethyl)pyridine (Aldrich) in 150 ml of benzene gave 35 g of an orange-brown, viscous oil. The oil was purified by chromatography (4.5×105 cm glass column; 500 g of silica gel; ethyl acetate-hexanes, 1:1). Desired fractions were combined and the solvents were evaporated under reduced pressure to yield 9.9 g (25%) of the title compound as a light-orange gum which is a (1:9) cis-trans isomeric mixture ($^{13}$C NMR).

The oil also yielded 6.8 g (17%) of the pure cis isomer and 7.1 g (18%) of the pure trans isomers. The total yield was 23.8 g (60%) with a (33:67) cis-trans population ratio.

| Analysis calculated for: | $C_{28}H_{24}N_2O_2S$: C, 74.31; H, 5.38; N, 6.19 |
|---|---|
| | Found: C, 73.73; H, 5.28; N, 6.17 |
| Analysis calculated for $C_{28}H_{24}N_2O_2S \cdot 0.1CH_3CO_2C_2H_5$ (ethyl acetate): | C, 73.93; H, 5.42; N, 6.07 |

EXAMPLE 77

2-(3-Phenoxyphenyl)-5-phenyl-3-[2-(2-pyridinyl)ethyl]-4-thiazolidinone trans isomer.

This compound (trans-isomer) was isolated (chromatography) in 18% yield in the purification of the product of Example 76. Rf (ethyl acetate-hexanes, 1:1; silica); 0.11.

| Analysis calculated for: | $C_{28}H_{24}N_2O_2S$: C, 74.31; H, 5.35; N, 6.19 |
|---|---|
| | Found: C, 73.37; H, 5.33; N, 6.12 |
| Analysis calculated for $C_{28}H_{24}N_2O_2S \cdot 0.15CH_3CO_2C_2H_5$ (ethyl acetate): | C, 73.75; H, 5.45; N, 6.01 |

EXAMPLE 78

5-Butyl-3-(4-phenylbutyl)-2-[3-(phenylmethoxy)phenyl]-4-thiazolidinone cis/trans (2:3) isomers.

This compound was prepared by the procedure used in Example 59. Thus, a solution of 12.7 g (0.06 mole) of 3-benzyloxybenzaldehyde (Aldrich), 9.1 g (0.060 mole) of 4-phenylbutylamine (98%, Aldrich), and 8.9 g (0.060 mole) of 2-mercaptohexanoic acid in 250 ml of benzene gave 24.3 g of a brown, viscous oil. The oil was purified by chromatography (4.5×105 cm glass column; 500 g of silica gel; ethyl acetate-hexanes, 1:16). Desired fractions were combined and the solvents evaporated under reduced pressure to yield 17.8 g (63%) of the title compound as a light-yellow, viscous oil which is a (2:3) cis-trans isomeric mixture ($^{13}$C NMR).

| Analysis calculated for: | $C_{30}H_{35}NO_2S$: C, 76.07; H, 7.45; N, 2.96 |
|---|---|
| | Found: C, 75.08; H, 7.36; N, 2.94 |
| Analysis calculated for $C_{30}H_{35}NO_2S \cdot 0.06CH_2Cl_2$: | C, 75.25; H, 7.59; N, 2.92 |

EXAMPLE 79

5-Butyl-2-(3-phenoxyphenyl)-3-phenyl-4-thiazolidinone cis isomer.

This compound was prepared by the procedure used in Example 59. Thus, 10.0 g (0.05 mole) of 3-phenoxybenzaldehyde (Fluka), 4.7 g (0.05 mole) of aniline and 7.5 g (0.05 mole) of 2-mercaptohexanoic acid in 250 ml of benzene gave 23.5 g of a viscous, oily residue. The oil was purified by chromatography (5×90 cm glass column; 550 g of silica gel; ethyl acetate-hexanes, 1:20, then ethyl acetate-hexanes, 1:1). Desired fractions were combined and the solvents evaporated under reduced pressure to give 5.0 g of a solid. The solid was recrystallized from isopropyl ether to yield 3.7 g (18%) of the title compound (cis isomer) as a white solid, mp 73°–75° C. Rf (ethyl acetate-hexanes, 1:4; silica): 0.53.

Also obtained by the purification was 6.5 g (32%) of the pure trans isomer (Example 80). The total yield was 10.2 g (50%) with a 36:64 cis-trans population ratio.

| Analysis calculated for: | $C_{25}H_{25}NO_2S$: C, 74.41; H, 6.24; N, 3.47 |
|---|---|
| | Found: C, 74.51; H, 6.24; N, 3.50 |

EXAMPLE 80

5-Butyl-2-(3-phenoxyphenyl)-3-phenyl-4-thiazolidinone trans isomer.

This compound was isolated (chromatography) in 32% yield as the trans isomer (yellow, viscous oil) in the preparation of Example 79. Rf (ethyl acetate-hexanes, 1:4; silica): 0.46.

| Analysis calculated for: | $C_{25}H_{25}NO_2S$: C, 74.41; H, 6.24; N, 3.47 |
|---|---|
| | Found: C, 74.15; H, 6.22; N, 3.50 |

EXAMPLE 81

5-Butyl-N,N-dimethyl-4-oxo-2-(3-phenoxyphenyl)-3-thiazolidineheptanamide hemihydrate cis/trans (1:3) isomers.

A mixture of 9.5 g (0.021 mole) of 5-butyl-4-oxo-2-(3-phenoxyphenyl)-3-thiazolidineheptanoic acid, cis-trans and 80 ml of thionyl chloride was stirred at ambient temperature for 3 hr. The excess thionyl chloride was removed under reduced pressure to give the acid chloride as a dark, gummy residue. A solution of this acid chloride in 100 ml of methylene chloride was added dropwise (20 min) to 150 ml of stirred, cooled (−15° C., dry ice-acetone bath) dimethylamine liquid. The mixture was stirred at ambient temperature overnight. The reaction mixture was partitioned between 200 ml of 2N hydrochloric acid solution and 300 ml of ethyl ether. The ether layer was washed successively with 200 ml of 2N hydrochloric acid, two 200 ml portions of water, dried (magnesium sulfate), and the solvent was evaporated under reduced pressure to give 7.6 g of a viscous residue. The residue was purified by high pressure liquid chromatography (Waters Associates PrepLC/System 500A; PrepPak ® 500 silica; ethyl acetate-hexanes, 2:1; flow rate 150 ml/min). Desired fractions were combined and the solvents evaporated under reduced pressure to give 4.2 g (42%) of the title compound as an orange, viscous oil which is a (1:3) cis-trans isomeric mixture ($^{13}$C NMR).

Also obtained was 1.7 g (17%) of the cis isomer. Total yield: 5.9 g (58%) with a (47:53) cis-trans population ratio.

Analysis calculated for:
$C_{28}H_{38}N_2O_3S \cdot 0.5 H_2O$:  C, 68.40; H, 8.00; N, 5.70
Found: C, 68.25; H, 8.12; N, 5.64

EXAMPLE 82

5-Butyl-2-(3-phenoxyphenyl)-3-(6-phenylhexyl)-4-thiazolidinone cis/trans (45:55) isomers.

This compound was prepared by the procedure used in Example 59. Thus, a solution of 5.0 g (0.025 mole) of 3-phenoxybenzaldehyde (Fluka), 4.5 g (0.025 mole) of 6-phenylhexylamine [prepared in 48% yield (light-yellow liquid) from 2-(6-phenylhexyl)-1,3-dihydro-1,3-dioxo-2H-isoindole], and 3.8 g (0.026 mole) of 2-mercaptohexanoic acid in 250 ml of benzene gave 10.4 g (84%) of a yellow, viscous oil. The oil was purified by high pressure liquid chromatography (Waters Associates Prep LC/System 500A; PrepPak ® 500 silica gel; ethyl acetate-hexanes, 1:15; flow rate 150 ml/min). Desired fractions were combined and the solvents evaporated under reduced pressure to yield 7.5 g (60%) of the title compound as a pale-yellow, viscous oil which is a (45:55) cis-trans isomeric mixture ($^{13}$C NMR).

Analysis calculated for:   $C_{31}H_{37}NO_2S$:  C, 76.35; H, 7.65; N, 2.87
Found: C, 76.25; H, 7.71; N, 2.81

EXAMPLE 83

5-Butyl-2-(3-phenoxyphenyl)-4-thiazolidinone trans isomer.

This compound was prepared according to the procedure used in Example 58. Thus, a mixture of 25.4 g (0.128 mole) of 3-phenoxybenzaldehyde (Fluka), 19.1 g (0.129 mole) of 2-mercaptohexanoic acid and 7.2 g (0.075 mole) of ammonium carbonate in 300 ml of benzene gave a viscous, oily residue. The oil was purified by high pressure liquid chromatography (Waters Associates Prep LC/System 500A; PrepPak ® silica; ethyl acetate-hexanes, 1:4; flow rate 150 ml/min). Desired fractions were combined and the solvents evaporated under reduced pressure to give 4.9 g (11%) of white solid. The solid was recrystallized from benzene-petroleum ether (30°-60° C.) to yield 4.3 g of the title compound as fluffy, white needles, mp 96°-98° C., which is pure trans isomer ($^{13}$C NMR).

Also obtained was 26.0 g (70%) of a cis-trans mixture as an oily residue from the HPLC fractions. Total reaction yield: 23.1 g (55%) of cis-trans products.

Analysis calculated for:   $C_{19}H_{21}NO_2S$:  C, 69.69; H, 6.46; N, 4.28
Found: C, 69.72; H, 6.43; N, 4.28

EXAMPLE 84

5-Butyl-2-[4-(phenylmethoxy)phenyl]-4-thiazolidinone cis/trans (5:95) isomers.

A mixture of 25.0 g (0.118 mole) of 4-benzyloxyenzaldehyde (Aldrich), 18.8 g (0.127 mole) of 2-mercaptohexanoic acid and 7.1 g (0.074 mole) of ammonium carbonate in 300 ml of benzene was stirred and heated at reflux overnight utilizing a Dean-Stark trap. The reaction mixture was poured into a solution of 400 ml of water and 17 ml of concentrated ammonium hydroxide. The layers were separated and the organic layer was washed twice with 300 ml portions of water, dried (magnesium sulfate), and the solvent was evaporated under reduced pressure to give a viscous residue that solidified upon standing. The solid was recrystallized from methylene chloride 2-propanol to give 7.3 g (18%) of the title compound as a white solid, mp 95°-98° C.

Analysis calculated for:   $C_{20}H_{23}NO_2S$:  C, 70.35; H, 6.79; N, 4.10
Found: C, 70.61; H, 6.77; N, 3.84

EXAMPLE 85

5-Butyl-3-[(4-methoxyphenyl)methyl]-2-(3-phenoxyphenyl)-4-thiazolidinone cis/trans (1:2) isomers.

A solution of 29.7 g (0.15 mole) of 3-phenoxybenzaldehyde (Fluka) and 21.0 g (0.15 mole) of 4-methoxybenzylamine (98%, Aldrich) in 200 ml of benzene was stirred and heated at reflux for 1.5 hr utilizing a Dean-Stark trap. To this reaction mixture was added 22.2 g (0.15 mole) of 2-mercaptohexanoic acid and the heating and stirring were continued for 15 hr. The mixture was then stirred at ambient temperature for 60 hr. The reaction mixture was poured into a solution of 400 ml of water and 20 ml of concentrated ammonium hydroxide. The layers were separated and the organic layer was washed with four 300 ml portions of water, dried (magnesium sulfate) and the solvent evaporated under reduced pressure to give 71.3 g of an orange, viscous oil. The oil was purified by chromatography (4.5 × 105 cm glass column: 520 g of silica gel; ethyl acetate-hexanes, 1:12). Desired fractions were combined and the solvents evaporated under reduced pressure to give 48.7 g (73%) of a yellow, viscous oil. A 1.6 g sample of this compound was further purified by high pressure liquid chromatography (Waters Associates Prep LC/System 500A; PrepPak ® 500 silica; ethyl acetate hexanes, 1:12; flow rate 150 ml/min). Fractions containing the product were combined and the solvents evaporated under reduced pressure to give 1.5 g of the title compound as a light-yellow gum which is a (1:2) cis-trans isomeric mixture ($^{13}$C NMR).

Analysis calculated for:   $C_{27}H_{29}NO_3S$:  C, 72.45; H, 6.53; N, 3.13
Found: C, 72.20; H, 6.49; N, 3.16

TABLE 1

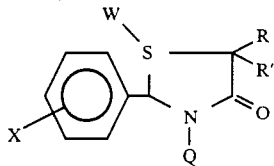

| Ex. No. | X | W | R | R' | Q | Isomer |
|---|---|---|---|---|---|---|
| 1 | 3-OC$_6$H$_5$ | — | H | —C$_4$H$_9$ | —(CH$_2$)$_4$C$_6$H$_5$ | cis/trans |
| 2 | 3-OC$_6$H$_5$ | — | H | —C$_4$H$_9$ | 4-OH—C$_6$H$_4$— | cis/trans |
| 3 | 3-OC$_6$H$_5$ | — | H | —C$_4$H$_9$ | 4-OH—C$_6$H$_4$— | cis |
| 4 | 3-OC$_6$H$_5$ | — | H | —C$_4$H$_9$ | 4-OH—C$_6$H$_4$— | trans |
| 5 | 3-OC$_6$H$_5$ | — | H | —C$_4$H$_9$ | 4-[C(O)—OC$_2$H$_5$]C$_6$H$_4$—(CH$_2$)$_4$— | trans |
| 6 | 3-OC$_6$H$_5$ | — | H | —C$_4$H$_9$ | 4-[C(O)—OC$_2$H$_5$]C$_6$H$_4$—(CH$_2$)$_4$— | cis |
| 7 | 3-OC$_6$H$_5$ | — | H | —CH$_3$ | —(CH$_2$)$_4$C$_6$H$_5$ | cis/trans |
| 8 | 3-C(O)C$_6$H$_5$ | — | H | —C$_4$H$_9$ | —(CH$_2$)$_4$C$_6$H$_5$ | cis/trans |
| 9 | 3-OC$_6$H$_5$ | — | H | —C$_6$H$_5$ | —(CH$_2$)$_4$C$_6$H$_5$ | cis |
| 10 | 3-OC$_6$H$_5$ | — | H | —C$_6$H$_5$ | —(CH$_2$)$_4$C$_6$H$_5$ | trans |
| 11 | 3-OC$_6$H$_5$ | — | CH$_3$ | —CH$_3$ | —(CH$_2$)$_4$C$_6$H$_5$ | — |
| 12 | 3-OC$_6$H$_5$ | — | H | —CH(CH$_3$)$_2$ | —(CH$_2$)$_4$C$_6$H$_5$ | cis/trans |
| 13 | 3-OC$_6$H$_5$ | — | H | —C$_6$H$_5$ | 4OH—C$_6$H$_5$— | cis/trans |
| 14 | 3-OC$_6$H$_5$ | — | H | —C$_4$H$_9$ | —(CH$_2$)$_3$C$_6$H$_5$ | cis |
| 15 | 3-OC$_6$H$_5$ | — | H | —C$_4$H$_9$ | —(CH$_2$)$_3$C$_6$H$_5$ | cis/trans |
| 16 | 3-OC$_6$H$_5$ | — | H | —C$_4$H$_9$ | —(CH$_2$)$_3$C$_6$H$_5$ | trans |
| 17 | 3-OC$_6$H$_5$ | — | H | —C$_4$H$_9$ | —(CH$_2$)$_2$C$_6$H$_5$ | cis/trans |
| 18 | 3-OC$_6$H$_5$ | — | H | —C$_4$H$_9$ | —(CH$_2$)$_2$-2-(C$_5$H$_4$N) | cis/trans |
| 19 | 3-OC$_6$H$_5$ | — | H | —C$_4$H$_9$ | —CH$_2$C$_6$H$_5$— | cis/trans |
| 20 | 3-OC$_6$H$_5$ | — | H | —C$_4$H$_9$ | 4-OH-3-[C(O)OCH$_3$]C$_6$H$_3$— | trans |
| 21 | 3-C(O)C$_6$H$_5$ | — | H | —C$_4$H$_9$ | 4-OH—C$_6$H$_5$— | cis |
| 22 | 3-C(O)C$_6$H$_5$ | — | H | —C$_4$H$_9$ | 4-OH—C$_6$H$_5$— | trans |
| 23 | 3-OC$_6$H$_5$ | — | H | —C$_4$H$_9$ | 4-OH-3-[C(O)OCH$_3$]C$_6$H$_3$— | trans |
| 24 | 3-OC$_6$H$_5$ | — | H | —C$_4$H$_9$ | 4-[C(O)OC$_2$H$_5$]—C$_6$H$_4$— | cis |
| 25 | 3-OC$_6$H$_5$ | — | H | —C$_4$H$_9$ | 4-[C(O)OC$_2$H$_5$]—C$_6$H$_4$— | trans |
| 26 | 3-C(O)C$_6$H$_5$ | — | H | —C$_4$H$_9$ | 4-OH-3[C(O)OCH$_3$]C$_6$H$_3$— | cis |
| 27 | 3-C(O)C$_6$H$_5$ | — | H | —C$_4$H$_9$ | 4-OH-3[C(O)OCH$_3$]C$_6$H$_3$— | cis/trans |
| 28 | 3-OC$_6$H$_5$ | — | H | —C$_4$H$_9$ | 4-OH-3[C(O)OH]C$_6$H$_4$— | cis/trans |
| 29 | 3-OC$_6$H$_5$ | — | H | —C$_4$H$_9$ | 4-[C(O)OC$_2$H$_5$]—C$_6$H$_4$—O—(CH$_2$)$_3$— | cis/trans |
| 30 | 3-OC$_6$H$_5$ | — | H | —C$_4$H$_9$ | 4-[C(O)OH]C$_6$H$_4$O(CH$_2$)$_3$— | cis/trans |
| 31 | 3-OC$_6$H$_5$ | — | H | —C$_4$H$_9$ | 4-[C(O)OC$_2$H$_5$]C$_6$H$_4$O(CH$_2$)$_3$— | trans |
| 32 | 3-OC$_6$H$_5$ | — | H | —C$_4$H$_9$ | 4-[C(O)OC$_2$H$_5$]C$_6$H$_4$O(CH$_2$)$_3$— | cis |
| 33 | 3-C(O)C$_6$H$_5$ | — | H | —C$_4$H$_9$ | 4-[C(O)OC$_2$H$_5$]C$_6$H$_4$O(CH$_2$)$_3$— | cis/trans |
| 34 | 3-C(O)C$_6$H$_5$ | — | H | —C$_4$H$_9$ | 4-[C(O)OH]C$_6$H$_4$O(CH$_2$)$_3$— | cis/trans |
| 35 | 3-OC$_6$H$_5$ | — | H | —C$_4$H$_9$ | C$_2$H$_5$OC(O)(CH$_2$)$_7$— | cis/trans |
| 36 | 3-OC$_6$H$_5$ | — | H | —C$_4$H$_9$ | 2-OCH$_3$-4-[-CH$_2$C(O)OC$_2$H$_5$]—C$_6$H$_3$—O(CH$_2$)$_3$— | cis/trans |
| 37 | 3-OC$_6$H$_5$ | — | H | —C$_4$H$_9$ | 2-OCH$_3$-4-[C(O)OCH$_3$]C$_6$H$_3$—O(CH$_2$)$_3$— | cis |
| 38 | 3-OC$_6$H$_5$ | — | H | —C$_4$H$_9$ | OHC(O)(CH$_2$)$_7$— | cis/trans |
| 39 | 3-OC$_6$H$_5$ | — | H | —C$_4$H$_9$ | 2-OCH$_3$-4-[C(O)OH]C$_6$H$_3$—O(CH$_2$)$_3$— | cis/trans |
| 40 | 3-OC$_6$H$_5$ | — | H | —C$_4$H$_9$ | 2-OCH$_3$-4-(CH$_2$C(O)OH)—O(CH$_2$)$_3$— | cis/trans |
| 41 | 3-OC$_6$H$_5$ | — | H | —C$_4$H$_9$ | OHC(O)(CH$_2$)$_2$— | cis/trans |
| 42 | 3-OC$_6$H$_5$ | — | H | —C$_4$H$_9$ | OHC(O)CH$_2$— | cis/trans |
| 43 | 3-OC$_6$H$_5$ | — | H | —C$_4$H$_9$ | OHC(O)(CH$_2$)$_5$— | cis/trans |
| 44 | 3-OC$_6$H$_5$ | — | H | —C$_4$H$_9$ | C$_2$H$_5$OC(O)(CH$_2$)$_4$— | cis |
| 45 | 3-OC$_6$H$_5$ | — | H | —C$_4$H$_9$ | OHC(O)CH$_2$]$_4$— | cis/trans |
| 46 | 3-OC$_6$H$_5$ | — | H | —C$_4$H$_9$ | OHC(O)CH$_2$]$_{10}$— | cis/trans |
| 47 | 3-OC$_6$H$_5$ | — | H | —C$_4$H$_9$ | 4-[C$_2$H$_5$OC(O)]—C$_6$H$_4$—CH$_2$— | cis/trans |
| 48 | 3-OC$_6$H$_5$ | — | H | —C$_4$H$_9$ | C$_2$H$_5$OC(O)(CH$_2$)$_{10}$— | cis/trans |
| 49 | 3-OC$_6$H$_5$ | — | H | —C$_4$H$_9$ | C$_2$H$_5$OC(O)(CH$_2$)$_3$— | cis |
| 50 | 3-OC$_6$H$_5$ | — | H | —C$_4$H$_9$ | C$_2$H$_5$OC(O)(CH$_2$)$_3$ | cis/trans |
| 51 | 3-OC$_6$H$_5$ | — | H | —C$_4$H$_9$ | C$_2$H$_5$OC(O)(CH$_2$)$_5$ | cis |
| 52 | 3-OC$_6$H$_5$ | — | H | —C$_4$H$_9$ | C$_2$H$_5$OC(O)(CH$_2$)$_5$ | trans |
| 53 | 3-OC$_6$H$_5$ | — | H | —C$_4$H$_9$ | C$_2$H$_5$OC(O)(CH$_2$)$_5$ | cis/trans |
| 54 | 3-OC$_6$H$_5$ | — | H | —C$_4$H$_9$ | OHC(O)CH$_2$]$_3$— | cis/trans |

TABLE 1-continued

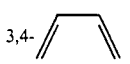

| Ex. No. | X | W | R | R' | Q | Isomer |
|---|---|---|---|---|---|---|
| 55 | 3-OC$_6$H$_5$ | — | H | —C$_4$H$_9$ | C$_2$H$_5$OC(O)(CH$_2$)$_6$— | cis/trans |
| 56 | 3-OC$_6$H$_5$ | — | H | —C$_4$H$_9$ | OHC(O)CH$_2$]$_6$— | cis/trans |
| 57 | 3-OC$_6$H$_5$ | — | H | —C$_4$H$_9$ | 4-[HOC(O)]C$_6$H$_4$CH$_2$— | cis/trans |
| 58 | 4-C$_6$H$_5$ | — | H | —C$_4$H$_9$ | C$_6$H$_5$(CH$_2$)$_4$— | cis/trans |
| 59 | 3-OC$_6$H$_5$ | — | H | —C$_4$H$_9$ | 4OHC$_6$H$_4$—(CH$_2$)$_2$— | cis/trans |
| 60 | 3-OC$_6$H$_5$ | — | H | —C$_4$H$_9$ | C$_6$H$_5$(CH$_2$)$_5$— | cis/trans |
| 61 | 3,4- 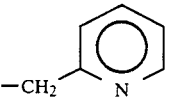 | — | H | —C$_4$H$_9$ | C$_6$H$_5$(CH$_2$)$_4$— | cis/trans |
| 62 | 4-OCH$_2$C$_6$H$_5$ | — | H | —C$_4$H$_9$ | C$_6$H$_5$(CH$_2$)$_4$— | cis/trans |
| 63 | 4-OC$_6$H$_5$ | — | H | —C$_4$H$_9$ | C$_6$H$_5$(CH$_2$)$_4$— | cis/trans |
| 64 | 3-OC$_6$H$_5$ | — | H | —C$_4$H$_9$ | 4-OH—C$_6$H$_4$CH$_2$— | cis/trans |
| 65 | 3-OC$_6$H$_5$ | — | H | —C$_4$H$_9$ | 4[HOC(O)CH$_2$O]C$_6$H$_4$CH$_2$— | cis/trans |
| 66 | 3-OC$_6$H$_5$ | O$_2$ | H | —C$_4$H$_9$ | C$_6$H$_5$(CH$_2$)$_4$— | cis/trans |
| 67 | 3-C(O)C$_6$H$_5$ | O$_2$ | H | —C$_4$H$_9$ | 4-[C$_2$H$_5$OC(O)]C$_6$H$_4$O—(CH$_2$)$_3$ | cis/trans |
| 68 | 3-OC$_6$H$_5$ | O$_2$ | H | —C$_4$H$_9$ | C$_2$H$_5$OC(O)(CH$_2$)$_5$— | cis/trans |
| 69 | 3-OC$_6$H$_5$ | O$_2$ | H | —C$_4$H$_9$ | C$_2$H$_5$OC(O)(CH$_2$)$_3$— | cis/trans |
| 70 | 3-OC$_6$H$_5$ | O$_2$ | H | —C$_4$H$_9$ | HOC(O)(CH$_2$)$_5$— | cis/trans |
| 71 | 3-OC$_6$H$_5$ | O | H | —C$_4$H$_9$ | HOC(O)(CH$_2$)$_5$— | — |
| 72 | 3-OC$_6$H$_5$ | — | H | —C$_4$H$_9$ | 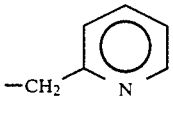 | cis |
| 73 | 3-OC$_6$H$_5$ | — | H | —C$_4$H$_9$ | 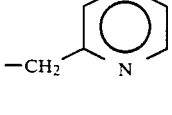 | cis/trans |
| 74 | 3-OC$_6$H$_5$ | — | H | —C$_4$H$_9$ | 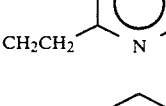 | trans |
| 75 | 3-OC$_6$H$_5$ | — | H | —C$_4$H$_9$ | 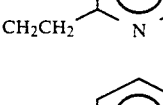 | cis |
| 76 | 3-OC$_6$H$_5$ | — | H | —C$_4$H$_9$ | 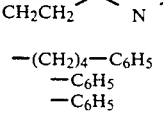 | cis/trans |
| 77 | 3-OC$_6$H$_5$ | — | H | —C$_4$H$_9$ | | trans |
| 78 | 3-OCH$_2$C$_6$H$_5$ | — | H | —C$_4$H$_9$ | —(CH$_2$)$_4$—C$_6$H$_5$ | cis/trans |
| 79 | 3-OC$_6$H$_5$ | — | H | —C$_4$H$_9$ | —C$_6$H$_5$ | cis |
| 80 | 3-OC$_6$H$_5$ | — | H | —C$_4$H$_9$ | —C$_6$H$_5$ | trans |
| 81 | 3-OC$_6$H$_5$ | — | H | —C$_4$H$_9$ | —(CH$_2$)$_6$—C(O)N(CH$_3$)$_2$ | cis/trans |
| 82 | 3-OC$_6$H$_5$ | — | H | —C$_4$H$_9$ | —(CH$_2$)$_6$—C$_6$H$_5$ | cis/trans |
| 83 | 3-OC$_6$H$_5$ | — | H | —C$_4$H$_9$ | H | trans |
| 84 | 4-OCH$_2$C$_6$H$_5$ | — | H | —C$_4$H$_9$ | H | cis/trans |
| 85 | 3-OC$_6$H$_5$ | — | H | —C$_4$H$_9$ | 4-CH$_3$OC$_6$H$_4$CH$_2$ | cis/trans |

PHARMACOLOGICAL TEST PROCEDURES

Cyclooxygenase Assay (See also Table 2)

Cyclooxygenase activity was determined polarigraphically with detergent solubilized, lipid-depleted sheep seminal vesical microsomes. Addition of test articles that inhibit cyclooxygenase, including reference standards, cause a decrease in the rate of oxygen consumption in the reactions. Cyclooxygenase activity is determined using the following procedures:

I. Preparation of Test Materials
1. Lipid-Depleted Sheep Seminal Vesicle Microsomal Powder. This preparation follows the procedure of G. Graff et al. J. Biol. Chem. 253, 7662 (1978).
2. Ammonium Arachidonate Solution. A 250 μL aliquot of 20.0 mM arachidonic acid in absolute ethanol and a 50-μL aliquot of concentrated ammonium hydroxide is placed into a test tube. The solvent and excess ammonium hydroxide is evaporated under a stream of nitrogen at room temperature. The ammonium arachidonate residue is dissolved in 500 μL of 100 mM 2-amino-2-hydroxymethyl-1,3-propanediol hydrochloride (Tris HCl) buffer (pH 8.0) by using a vortex mixer. The final concentration of ammonium arachidonate (working solution) is 10.0 mM.
3. Enzyme Buffer 100 mM Tris HCl (pH 8.0) containing 2.0 mM phenol, 5.0 mM ethylenediaminetetraacetic acid (EDTA), 5.0 mM diethyldithiocarbamic acid and 1.0% Tween 20.
4. Reaction Buffer 100 mM Tris HCl (pH 8.0) containing 2.0 μM hematin and 1.0 mM phenol (prepared daily).
5. Detergent Solubilized Lipid-depleted Sheep Seminal Vesicle Microsome Suspension. Ten mg (solid) of lipid-depleted microsomal powder from sheep seminal vesicles is suspended in 1.0 mL of enzyme buffer and kept at 4° C. until used. This lipid-depleted microsomal enzyme suspension shows no decline in PGH-synthase activity for up to 6 hr when kept at 4° C.
6. Solutions of Test (Formula I compound) or Reference Articles. Test and reference articles are dissolved in the reaction buffer prepared in 4) or a solvent that will not interfere with cyclooxygenase activity, e.g., dimethylsulfoxide, ethanol or acetone.

II. Cyclooxygenase Inhibition Assay

Three mL of the reaction buffer and 20 μL of the microsomal enzyme suspension are placed in a Yellow Springs Instrument (YSI) oxygen chamber where the temperature is maintained at 30° C. by means of a temperature controlled circulating water bath. Aliquots of the solutions containing ≦1.5 millimoles of Formula I compound (test article) or reference article [see 6) above] are added to the YSI chamber and incubated for 2 minutes. The reaction is initiated by addition of 30 μL of the 10 mM ammonium arachidonate solution and cyclooxygenase activity determined polarigraphically using an oxygen electrode by measuring the rate of oxygen consumption [Cook et al., Anal. Biochem 96 341–51 (1979) and Cook and Lands, Can. J. Biochem. 53, 1220–1231 (1975)].

Test, reference, and control articles were evaluated in triplicate. Cyclooxygenase activity was determined from the slope (mv/unit time) of the recorder tracing with 1 mV being proportional to a 2.34 μM change in oxygen concentration.

The $IC_{50}$ (concentration of test or reference article that inhibits the reaction by 50%) was calculated from cumulative plots relating the extent of inhibition of cyclooxygenase activity in control group assays to increasing concentrations of test article. Where no inhibition exists, the $IC_{50}$ is expressed as greater than the highest concentration of the drug tested.

5-Lipoxygenase Assay

The production of 5-HETE from arachidonic acid in human polymorphonuclear leukocytes stimulated by the calcium ionophore $A_{23187}$ (Calbiochemicals) was measured by reverse phase high pressure liquid chromatography. This procedure is a modification of the procedure of Sun and McGuire, PROSTAGLANDINS, 26, 211–221 (1983). Addition of substances to the test system that inhibit 5-lipoxygenases cause a decrease in the production of 5-HETE and is thus determined in comparison to reference and control articles also added to the reaction system.

Polymorphonuclear leukocytes were obtained from whole human blood by the procedure of Skoog and Beck, BLOOD, 11, 436–454 (1956). $1.5-2.0 \times 10^7$ PMN cells suspended in 1 mL of 10 mM sodium phosphate buffer (pH 7.4) containing 154 mM in sodium chloride and 55 mM D-glucose is incubated with a test or reference compound ($\leq 100$ μM, dissolved in ethanol or other solvent that does not interfere with the conversion of arachidonic acid to 5-HETE at 37° C. for 5 min. Twenty-five μL of calcium chloride solution (100 mM calcium chloride aqueous solution, adjusted to pH 7.4 with dilute sodium hydroxide) is added, followed by 3.3 μL of an ethanolic solution that is 0.80 mM in the calcium ionophore $A_{23187}$ and 12.1 mM in arachidonic acid. The tube is incubated for an additional 10 min at 37° C. and the incubations terminated by addition of 1.5 mL of acetone and cooling to 0° C. 13-Hydroxyoctadecatrienoic acid (13-HODT) (5 μL of 0.2 mM methanolic solution) is added for an internal reference standard. The tube is stored at $-20°$ C. under argon for 4–18 hr. Centrifugation at $1000 \times g$ for 10 min causes protein precipitate to form a pellet. The acetone layer is evaporated under a stream of nitrogen and the resultant lipid residue containing the arachidonic acid metabolites and 13-HODT is dissolved in 0.5 mL of methanol and stored at $-20°$ C. until analyzed by high-pressure liquid chromatography (HPLC).

For analysis, a 150-μL aliquot of the methanol solution is evaporated under a stream of argon. The residue is reconstituted with 100 μL of a 1:1 methanol-water mixture and sonified for 15–20 seconds and the mixture analyzed by HPLC ($C_{18}$ reversed phase Econophere column, methanol:water:acetic acid 79:25:0.2 v/v/v used for elution). Test, reference, and control articles are evaluated in duplicate. The inhibition is reported as that concentration which will inhibit by 50% the production of 5-HETE.

UV-Erythema in Guinea Pigs

I. Preparation of Formulation (cream)

All drugs tested were prepared by thoroughly incorporating 1.0 mg of the test article into 1 g of a pH 7.0 cream vehicle of the following composition.
  methyl glucose sesquistearate 1.6%
  methyl gluceth-20 sesquistearate 2.4%
  methyl gluceth 20 4.0% acetylated lanolin 2.0%
acetyl alcohol 5.0%
emulsifying wax, N.F. 5.0%
mineral oil (heavy), U.S.P. 1.0%
white petrolatum, U.S.P. 5.0%
glyceryl stearate 5.0%
stearic acid, U.S.P. 2.5%
sodium benzoate, N.F. 0.1%
sodium propionate 0.1%
magnesium aluminum silicate 1.5%
deionized water, pH 7.0 64.8%

The preparations were packed into 1-cc plastic syringes.

II. Pharmacological Assay

The backs of female, English short hair guinea pigs (250–500 g) were shaved and depilated with Nair ®. Control and treated groups each consisted of 5 animals, and selection of the animals and the control and treatment groups was achieved by random procedures. A rubber sheet with three one-half inch holes spaced one-half inch apart was draped over backs of the guinea pigs. The guinea pigs were then exposed to ultraviolet (UV) light (Hanovia Model 10, ~650–800 $\mu W/cm^2$) for 15 seconds by holding the animals against the light source. Fifty $\mu L$ of the test drug or reference drug (indomethacin or bromfenac) preparation were immediately rubbed onto the skin, either on the area exposed to UV light or to an area adjacent to the UV light exposed skin. The degree of erythema for each exposed area was scored at various times following exposure according to the following scale:

0 = no erythema
1 = slight redness with faint outline
2 = moderate to marked redness with distinct outline The score was totaled for each guinea pig (maximum score is 6). The Dunnett's t-test was used to determine significant ($p \leq 0.05$) differences from the control (placebo treated) group. A test article which gives a composite score is the test group that is significantly lower than the control group. Dunnett's t-test is considered active, i.e. is given a positive (+) designation, as shown in Table 2, in the evaluation of compounds tested. Compounds receiving a negative (−) score were not significantly active at the concentration tested.

TABLE 2

Pharmacological Data of Certain Compounds of Formula I Compared to Controls

| Example | Cyclooxygenase IC$_{50}$ ($\mu M$) | 5-Lipoxygenase IC$_{50}$ ($\mu M$) | U.V. erythema IC$_{50}$ ($\mu M$) (+ = active − = inactive[a]) |
|---|---|---|---|
| 1 | 0.09 | >100 | + |
| 3 | 8 | 5 | N.T. |
| 5 | 0.07 | N.T. | N.T. |
| 6 | 0.05 | N.T. | N.T. |
| 7 | 1.4 | <20 | + |
| 8 | 0.01 | ~100 | + |
| 17 | 3.4 | 10 | − |
| 18 | 0.12 | 7.8 | N.T. |
| 22 | 2.2 | 6.4 | N.T. |
| 30 | 1.6 | 3.5 | N.T. |
| 45 | 9.3 | ~15 | + |
| 51 | 0.26 | ~15 | − |
| 55 | 1.0 | ~10 | N.T. |
| 59 | N.T. | N.T. | + |

TABLE 2-continued

Pharmacological Data of Certain Compounds of Formula I Compared to Controls

| Example | Cyclooxygenase IC$_{50}$ ($\mu M$) | 5-Lipoxygenase IC$_{50}$ ($\mu M$) | U.V. erythema IC$_{50}$ ($\mu M$) (+ = active − = inactive[a]) |
|---|---|---|---|
| 83 | 12 | <10 | − |

[a]See description for activity definition.
N.T. = Not tested

Pharmaceutical Compositions and Methods of Administration

Pharmaceutical compositions for transdermal administration to animals and humans are comprised of at least one of the compounds of Formula I as active agent and a carrier which is not unduly destabilizing to the active agent and which is non-toxic to the skin and allows delivery of the agent to the inflammed skin. The carrier may take any number of different forms such as creams and ointments, pastes, gels, foams.

The creams and ointments may be viscous liquid at semisolid emulsions of either the oil-in-water or water-in-oil type, preferably the oil-in-water type.

Pastes comprised of absorptive powders dispersed in petroleum or hydrophilic petroleum containing the active agent may be used.

The pharmaceutical preparation may be applied to the skin in any part of the body where the inflammed condition exists.

Any of the carriers may contain penetration enhancers, i.e., materials that have a direct effect on the permeability of the skin. The preferred creams Formulas A and B contain a large amount of water which is one type of penetration enhancer. Other suitable penetration enhancers are eugenol, dimethylformamide, dimethylsulfoxide, dimethylacetamide, N,N-diethyl-m-toluamide (DEET) and 1-dodecylazacycloheptan-2-one (Azone).

Examples of cream, gel, or paste preparations that can be used as a carrier for compounds of Formula I are listed hereinbelow. These are included as examples only and not meant to exclude other liquid, gel, or paste preparations that would be obvious to one skilled in the art.

| Cream Preparation - Formula A (Neutral pH = 7.0) | |
|---|---|
| Ingredients | Weight (grams) |
| 1. Oil Phase Composition | |
| Methyl glucose sesquistearate[a] | 16.0 |
| Methyl gluceth-20 sesquistearate[b] | 24.0 |
| Methyl gluceth-20[c] | 40.0 |
| Acetylated lanolin[d] | 20.0 |
| Cetearyl alcohol[e] | 50.0 |
| Emulsifying wax, N.F.[f] | 50.0 |
| Heavy mineral oil[g] | 10.0 |
| White petrolatum U.S.P.[h] | 50.0 |
| Glyceryl monostearate[i] | 50.0 |
| Stearic acid N.F.[j] | 25.0 |
| 2. Water Phase Composition | |
| 4-Hydroxybenzoic acid methyl ester[k] | 1.8 |
| 4-Hydroxybenzoic acid propyl ester[l] | 0.2 |
| Magnesium aluminum silicate[m] | 15.0 |
| Deionized water | 648.0 |
| Total | 1000.0 |
| 3. Active agent | variable |

Mixing procedure:

Mix oil phase ingredients (1. above) and warm to 80° C. until the mixture melts. Separately, warm preservatives and water to 85° C. to dissolve and add and disperse the magnesium aluminum silicate to form the water phase (2. above). Add the water phase to stirred oil phase at 85° C. to obtain oil-in-water-based cream. Evenly disperse active agent in desired proportion, usually up to 10 wt % in the cream.

| Cream Preparation - Formula B (Neutral pH = 7.0) | |
|---|---|
| Ingredients | Weight (grams) |
| 1. Oil Phase Composition | |
| Same as Formula A | Same as Formula A (335.0 g) |
| 2. Water Phase Composition | |
| Sodium benzoate** | 1.0 |
| Sodium propionate** | 1.0 |
| Deionized water | 632.0 |
| Magnesium aluminum silicate | 15.0 |
| Total | 984.0 |
| Total | 1000.0 |
| 3. Active agent | variable |

Footnotes to Formula A and B.
[a]Amerchol glucamate SSE-20 ® produced by Amerchol Corp., P.O. Box 351, Edison, NJ 08817.
[b]Amerchol glucamate SSE-20 ®, Amerchol Corp.
[c]Amerchol glucam ® - Amerchol Corp.
[d]Amerchol modulan ® - Amerchol Corp.
[e]Crodacol CS-50 ® produced by Croda. Inc., 51 Madison Avenue, N.Y., N.Y. 10010.
[f]Palorwax ® - Croda, Inc.
[g]Kaydol ® produced by Witco Chem. Corp., Sonneborn Div., 277 Park Avenue, N.Y., NY 10017.
[h]See the United States Pharmacopeia, 21st Ed. (1984).
[i]Cerasynt S.D. ® produced by Van Dyk & Co., Inc., Main and William Streets, Belleville, NJ 07109.
[j]See The National Formulary, 16th Ed.
[k]Methyl paraben, N.F. See The National Formulary, 16th Ed.
[l]Propyl paraben. See the National Formulary, 16th Ed.
[m]Veegum K ® produced by R. T. Vanderbilt Co., Inc., 30 Winfield Street, Norwalk, CT 06855.
*4-Hydroxybenzoic acid esters are effective preservatives at pH = 7.
**Sodium benzoate and sodium propionate are effective as preservative under acid conditions.

Mixing procedure:
Same as for Formula A.

| Hydrogel Preparation - Formula C | |
|---|---|
| Ingredients | Weight (grams) |
| Hydroxyethylcellulose, N.F.[a] | 20 |
| Water | 480 |
| Active agent of Formula I | variable |

Footnotes to Formula C
[a]Natrosol produced by Hercules, Inc., 910 Market Street, Wilmington, DE 19899.

Mixing procedure:
Warm the distilled water to about 80° C. Rapidly stir the water to create a vortex and add lump-free hydroxyethylcellulose to the vortex and continue stirring until a smooth viscous gel is obtained. The gel is poured into individual bottles which are then autoclaved at 121° C., 15 psig for 15 minutes. Active ingredient is added prior to test use by levigation Preparation of Petrolatum Ointment-Formula D Levigate known amount of active agent of Formula I in known amount of white petrolatum, U.S.P.

Advantageously the compositions are formulated to be dispensed as a cream or gel or foam that can be rubbed onto the skin or as an aerosol to be sprayed on the inflamed area of skin. It is only necessary that the active ingredient constitute an effective amount, i.e., such that a suitable effective dosage will be consistent with the dosage form employed. The exact individual dosages, as well as daily dosages, will of course be determined according to standard medical principles under the direction of a physician or veterinarian.

It is anticipated based on limited tests with animals, for example, Formula A above, application of a cream (pH 6.5-8.0) containing 3 to 10 wt % active agent (Formula I) in the amount so as to contain a total of 50-300 mg per 5-15 cm$^2$ area of skin will be sufficient to relieve pain and inflammation for several hours. Repeated application is contemplated. Delivery of similar amounts by other vehicles is also contemplated. However, the scope of the invention is not to be limited by these contemplations due to uncertainty in transposing from animal data.

What is claimed is:

1. A compound corresponding to the formula wherein:
R is hydrogen or loweralkyl;
R' is loweralkyl or phenyl optionally substituted with loweralkyl, loweralkoxy trifluoromethyl, nitro, or halo;
X is $-(CH_2)_{0-3}$-aryl, $-C(O)(CH_2)_{0-3}$-aryl, $-C(O)(CH_2)_{0-3}$-aryl, or $-CHOH-(CH_2)_{0-3}$-aryl, aryl is phenyl optionally substituted with loweralkyl loweraralkoxy, trifluoromethyl, nitro or halo;
W is oxygen;
Q is $-(alk^1)_{0-1}-(O)_{0-1}-(B)_{0-1}-(O)_{0-1}-(alk^2)_{0-1}-[C(O)Z]_{0-1}$;
B is Y is selected from hydrogen, loweralkyl, loweralkoxy, trifluoromethyl, nitro, or halo;
alk$^1$ and alk$^2$ are selected from the group consisting of loweralkylene or loweralkylene-loweralkyl and may be the same or different;
Z is $-OR^3$ or $-NR^4R^5$,
R$^3$ is hydrogen, loweralkyl or a pharmaceutically acceptable metal cation;
R$^4$ and R$^5$ are hydrogen or loweralkyl;
and when any of the groups within the definition of Q other than [C(O)Z] is a terminal group or all groups are absent, the valence is occupied by a hydrogen atom;
or the cis or trans stereoisomer or optically active isomer thereof or pharmaceutically acceptable acid addition salt which forms when a basic nitrogen moiety is present.

2. A compound of claim 1 which is 5-butyl-2-(3-phenoxyphenyl)-3-(4-phenylbutyl)-4-thiazolidinone cis-trans (1:3).

3. A compound of claim 1 which is 5-butyl-3-(4-hydroxyphenyl)-2-(3-phenoxyphenyl)-4-thiazolidinone cis isomer.

4. A compound of claim 1 which i 4-[4-[5-butyl-4-oxo-2-(3-phenoxyphenyl)-3-thiazolidinyl]butyl]benzoic acid ethyl ester trans isomer.

5. A compound of claim 1 which i 4-[4-[5-butyl-4-oxo-2-(3-phenoxyphenyl)-3-thiazolidinyl]butyl]benzoic acid ethyl ester cis isomer.

6. A compound of claim 1 which i 5-methyl-2-(3-phenoxyphenyl)-3-(4-phenylbutyl)-4-thiazolidinone cis-trans (2:3).

7. A compound of claim 1 which i 2-(3-benzoylphenyl)-5-butyl-3-(4-phenylbutyl)-4-thiazolidinone cis-trans (2:3).

8. A compound of claim 1 which is 5-butyl-2-(3-phenoxyphenyl)-3-(2-phenylethyl)-4-thiazolidinone.

9. A compound of claim 1 which is 2-(3-benzoylphenyl)-5-butyl-3-(4-hydroxyphenyl)-4-thiazolidinone cis isomer.

10. A compound of claim 1 which is 4-[3-[5-butyl-4-oxo-2-(3-phenoxyphenyl)-3-thiazolidinyl]propoxy]benzoic acid cis trans (2:3).

11. A compound of claim 1 which is 5-butyl-4-oxo-2-(3-phenoxyphenyl)-3-thiazolidinepentanoic acid cis/trans 40:60.

12. A compound of claim 1 which is 5-butyl-4-oxo-2-(3-phenoxyphenyl)-3-thiazolidinehexanoic acid ethyl ester cis isomer.

13. A compound of claim 1 which is 5-butyl-4-oxo-2-(3-phenoxyphenyl)-3-thiazolidineheptanoic acid ethyl ester cis/trans 1:1.

14. A compound of claim 1 which is 5-butyl-3-[2-(4-hydroxyphenyl)ethyl]-2-(3-phenoxyphenyl)-4-thiazolidinone cis/trans 2:3.

15. A compound of claim 1 which is 5-butyl-2-(3-phenoxyphenyl)-4-thiazolidinone trans isomer.

16. A method of treating inflammed conditions of the skin by topical application of a pharmaceutical dosage form comprised of an effective amount for treating inflammed conditions of a substituted 4-thiazolidinone corresponding to the formula:

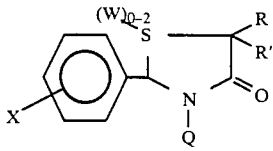

wherein:
R is hydrogen or loweralkyl;
R' is loweralkyl or phenyl optionally substituted with loweralkyl, loweralkoxy, trifluoromethyl, nitro or halo;
X is —(CH$_2$)$_{0-3}$-aryl, —O(CH$_2$)$_{0-3}$-aryl, —C(O)(CH$_2$)$_{0-3}$-aryl, or —CHOH—(CH$_2$)$_{0-3}$-aryl optionally substituted with loweralkyl, loweralkoxy, trifluoromethyl, nitro or halo;
W is oxygen;
Q is —(alk$^1$)$_{0-1}$—(O)$_{0-1}$—(B)$_{0-1}$—(O)$_{0-1}$—(alk$^2$)$_{0-1}$—[C(O)Z]$_{0-1}$;
B is

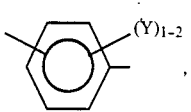

Y is selected from hydrogen, loweralkyl, loweralkoxy, trifluoromethyl, nitro, or halo;
alk$^1$ and alk$^2$ are selected from the group consisting of loweralkylene or loweralkylene-loweralkyl and may be the same or different;
Z is —OR$^3$ or —NR$^4$R$^5$,
R$^3$ is hydrogen, loweralkyl or a pharmaceutically acceptable metal cation;
R$^4$ and R$^5$ are hydrogen or loweralkyl;
and when any of the groups within the definition of Q other than [C(O)Z] is a terminal group or all groups are absent, the valence is occupied by a hydrogen atoms;
or the cis or trans stereoisomer or optically active isomer thereof or pharmaceutically acceptable acid addition salt which forms when a basic nitrogen moiety is present.

17. The method of claim 16 wherein the compound used is 5-butyl-2-(3-phenoxyphenyl)-3-(4-phenylbutyl)-4-thiazolidinone cis-trans (1:3).

18. The method of claim 16 wherein the compound used is 5-butyl-3-(4-hydroxyphenyl)-2-(3-phenoxyphenyl)-4-thiazolidinone cis isomer.

19. The method of claim 16 wherein the compound used is 4-[4-[5-butyl-4-oxo-2-(3-phenoxyphenyl)-3-thiazolidinyl]butyl]benzoic acid ethyl ester trans isomer.

20. The method of claim 16 wherein the compound used is 4-[4-[5-butyl-4-oxo-2(3-phenoxyphenyl)-3-thiazolidinyl]butyl]benzoic acid ethyl ester cis isomer.

21. The method of claim 16 wherein the compound used is 5-methyl-2-(3-phenoxyphenyl)-3-(4-phenylbutyl)-4-thiazolidinone cis-trans (2:3).

22. The method of claim 16 wherein the compound used is 2-(3-benzoylphenyl)-5-butyl-3-(4-phenylbutyl)-4-thiazolidinone cis-trans (2:3).

23. The method of claim 16 wherein the compound used is 5-butyl-2-(3-phenoxyphenyl)-3-(2-phenylethyl)-4-thiazolidinone.

24. The method of claim 16 wherein the compound used is 2-(3-benzolyphenyl)-5-butyl-3-(4-hydroxyphenyl)-4-thiazolidinone cis isomer.

25. The method of claim 16 wherein the compound used is 4-[3-[5-butyl-4-oxo-2-(3-phenoxyphenyl)-3-thiazolidinyl]propoxy]benzoic acid cis trans (2:3).

26. The method of claim 16 wherein the compound used is 5-butyl-4-oxo-2-(3-phenoxyphenyl)-3-thiazolidinepentanoic acid cis/trans 40:60.

27. The method of claim 16 wherein the compound used is 5-butyl-4-oxo-2-(3-phenoxyphenyl)-3-thiazolidinehexanoic acid ethyl ester cis isomer.

28. The method of claim 16 wherein the compound used is 5-butyl-4-oxo-2-(3-phenoxyphenyl)-3-thiazolidineheptanoic acid ethyl ester cis/trans 1:1.

29. The method of claim 16 wherein the compound used is 5-butyl-3-[2-(4-hydroxyphenyl)ethyl]-2-(3-phenoxyphenyl)-4-thiazolidinone cis/trans 2:3.

30. The method of claim 16 wherein the compound used is 5-butyl-2-(3-phenoxyphenyl)-4-thiazolidinone trans isomer.

31. A pharmaceutical composition comprising a. an effective amount for treating inflammed conditions of the skin by topical application of a compound corresponding to the formula

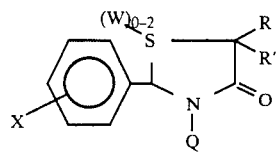

wherein:

R is hydrogen or loweralkyl;

R' is loweralkyl or phenyl optionally substituted with loweralkyl, loweralkoxy, trifluoromethyl, nitro or halo;

Y is selected from hydrogen, loweralkyl, loweralkoxy, trifluoromethyl, nitro, or halo;

$alk^1$ and $alk^2$ are selected from the group consisting of loweralkylene or loweralkylene-loweralkyl and may be the same or different;

X is —$(CH_2)_{0-3}$-aryl, —$O(CH_2)_{0-3}$-aryl, —C-$(O)(CH_2)_{0-3}$-aryl, or —CHOH— $(CH_2)_{0-3}$-aryl aryl is 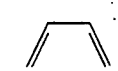

phenyl optionally substituted with loweralkyl, loweralkoxy, trifluoromethyl, nitro or halo;

W is oxygen;

Q is —$(alk^1)_{0-1}$—$(O)_{0-1}$—$(B)_{0-1}$—$(O)_{0-1}$—$(alk^2)_{0-1}$—$[C(O)Z]_{0-1}$;

B is

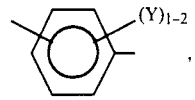

Z is —$OR^3$ or —$NR^4R^5$, $R^3$ is hydrogen, loweralkyl or a pharmaceutically acceptable metal cation;

$R^4$ and $R^5$ are hydrogen or loweralkyl; and when any of the groups within the definition of Q other than [C(O)Z] is a terminal group or all groups are absent the valence is occupied by a hydrogen atom;

or the cis or trans stereoisomer or optically active isomer thereof and pharmaceutically acceptable acid addition salt which forms when a basic nitrogen moiety is present, and b. a pharmaceutically acceptable carrier.

* * * * *